United States Patent [19]
Kuhn et al.

[11] Patent Number: 5,453,517
[45] Date of Patent: Sep. 26, 1995

[54] REACTIVE DERIVATIVES OF BAPTA USED TO MAKE ION-SELECTIVE CHELATORS

[75] Inventors: Michael A. Kuhn; Richard P. Haugland, both of Eugene, Oreg.

[73] Assignee: Molecular Probes, Inc., Eugene, Oreg.

[21] Appl. No.: 843,360

[22] Filed: Feb. 25, 1992

[51] Int. Cl.$^6$ ............... C07D 311/88; C07D 265/30; C08B 37/02; C07H 23/00
[52] U.S. Cl. ............... 549/227; 544/162; 544/163; 544/164; 544/165; 544/167; 544/168; 544/169; 546/37; 548/259; 548/545; 548/546; 548/547; 548/548; 549/223; 560/44; 560/358
[58] Field of Search ............... 544/162–165, 544/167–169; 548/259, 545–548; 546/37; 549/223, 227; 560/44, 358; 562/426, 434, 435, 437, 438, 440, 457; 564/27, 211, 214, 305; 536/51, 121, 123

[56] References Cited

U.S. PATENT DOCUMENTS

| | | |
|---|---|---|
| 4,603,209 | 7/1986 | Tsien et al. ............... 548/236 |
| 4,707,440 | 11/1987 | Stavianopoulos ............... 435/6 |
| 4,849,362 | 7/1989 | DeMarinis et al. ............... 436/63 |
| 5,049,673 | of/1991 | Tsien et al. ............... 548/236 |

OTHER PUBLICATIONS

Analyt. Biochem. 137, 335 (1984).
Science 209, 295 (1980).
Proc. Nat'l Acad. Sci. 83, 4277 (1986).
Meares, et al., Analyt. Biochem. 142, 68 (1984).
Cummins, et al., Bioconjugate Chem. 2, 180 (1991).
Cell Calcium 10, 491 (1989).
Heath in Methods in Enzymology 149, 111 (1987).
J. Med. Chem. 17, 1304 (1974).
J. Med. Chem. 22, 1019 (1979).
Biochem. 19, 2396 (1980) [Article Not Currently Available].
*Intracellular Measurements of Ion Activities,* Ann. Rev. Biophys. Bioeng. 12, 91 (1983) [Article Not Currently Available].
Methods in Enzymology 172, 230 (1989).

*Primary Examiner*—Cecilia Tsang
*Attorney, Agent, or Firm*—Allegra Helfenstein; Anton E. Skaugset

[57] ABSTRACT

The invention relates to fluorescent and/or reactive derivatives of 1,2-bis-(2-aminophenoxyethane)-N,N,N',N'-tetraacetic acid (BAPTA) according to the formula:

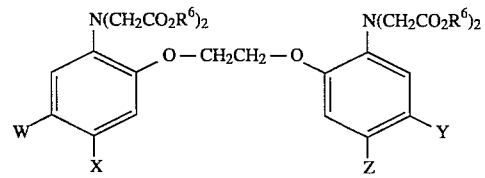

where at least one of W and X is a functional group, with or without a spacer, that terminates in an alcohol or phenol, a thiol, a haloacetamide, an alkyl halide, an amine or aniline, a carboxylic acid, an anhydride, an isocyanate, an isothiocyanate, a maleimide, or an activated ester. The BAPTA-like molecule may be further substituted, one or more times, by additional functional groups with or without spacers or by $CH_3$, $NO_2$, $CF_3$, F, Cl, Br, I, or carboxylic acid derivatives or pharmaceutically acceptable salts thereof, or by indolyl or benzofuran fluorophores. The functional groups allow for subsequent covalent attachment of one or more oxygen heterocycle fluorophores (e.g. fluorescein, coumarin, rhodamine); or polymolecular assemblies (e.g. gel and resin polymers, polysaccharides, polypeptides, nucleic acids, and liposomes); or combinations thereof.

67 Claims, 9 Drawing Sheets

REACTIVE DERIVATIVES OF BAPTA USED TO MAKE ION-SELECTIVE CHELATORS

This invention was made with Government support under GM 37347 awarded by the National Institutes of Health. The Government has certain rights in this invention.

FIELD OF THE INVENTION

This invention relates to fluorescent and reactive chelators used to make indicators and polymolecular assemblies that selectively bind to polyvalent metal ions. In particular, the invention relates to fluorescent and/or reactive derivatives of 1,2-bis-(2-aminophenoxyethane)-N,N,N',N'-tetraacetic acid (BAPTA) that are covalently attached to fluorophores and/or polymolecular assemblies, and novel intermediates in the synthesis thereof.

BACKGROUND OF THE INVENTION

Metals play an important role in biological systems in regulating enzyme activity, protein structure, and cellular signalling. Metals can also have a deleterious effect when present in excess of bodily requirements or capacity to excrete. A large number of natural and synthetic materials are known to selectively or non-selectively bind to or chelate metals. Ion chelators are commonly used in solution for in vivo control of ionic concentrations and detoxification of excess metals, and as in vitro buffers and optical indicators of ionic transients.

In addition, metal chelators immobilized on a carrier have been described for use in 1) removal or selective concentration of polyvalent metal ions from aqueous solutions and from metal binding sites of proteins; 2) attachment to antibodies and conjugation with gamma emitters such as $Gd^{3+}$ and $In^{3+}$ for use in delivering deadly doses of radiation to tumor cells (J. MED. CHEM. 17, 1304 (1974); J. MED. CHEM. 22, 1019 (1979)); 3) time resolved fluorescence immunoassays that usually use $Tb^{3+}$ or $Eu^{3+}$ complexes (ANALYT. BIOCHEM. 137, 335 (1984)); 4) radioimmunoassays; 5) gamma camera and NMR imaging (SCIENCE 209, 295 (1980); PROC. NAT'L ACAD. SCI. 83, 4277 (1986)); and 6) structural studies of the microenvironment and dynamic properties of proteins, membranes and nucleic acids.

Virtually all of the chelator compounds used for these applications have been derivatives of iminodiacetic acid (IDA as in Chelex™ ion-selective resins) or related amine aliphatic compounds such as ethylenediamine tetraacetic acid (EDTA), diethylenetriaminepentaacetic acid (DTPA) or of ethylene glycol-bis(β-aminoethyl ether)-N,N,N',N'-tetraacetic acid (EGTA). Several reactive derivatives of EDTA and DTPA are known. See e.g. Meares, et al., ANALYT. BIOCHEM. 142, 68 (1984); Cummins, et al., BIOCONJUGATE CHEM. 2, 180 (1991). Of the IDA-like indicators, EGTA has the highest selectivity and affinity for $Ca^{2+}$ versus $Mg^{2+}$ and other polyvalent metals. The IDA, EDTA, DTPA and EGTA chelators with aliphatic amine groups, however, are all protonated at physiological pH (about pH 7), which significantly decreases their affinity. The need exists for a polymolecular carrier incorporating a highly selective ion chelator that does not show a significant decrease in affinity at physiological pH.

Among the highest affinity and most selective of the chelators, especially for $Ca^{2+}$, have been derivatives of 1,2-bis-(2-aminophenoxyethane)-N,N,N',N'-tetraacetic acid (BAPTA) originally described by Tsien, BIOCHEM. 19, 2396 (1980). BAPTA has a high affinity for $Ca^{2+}$ and certain other polyvalent metals such as the lanthanides $Tb^{3+}$, $Eu^{3+}$, $Gd^{3+}$, $Ln^{3+}$, and $Zn^{2+}$, $Pb^{2+}$, $Mn^{2+}$, $Cd^{2+}$ and $Ba^{2+}$. Unlike the aliphatic amine chelators, the metal affinity of BAPTA chelators is about the same at pH 7 as above pH 7. In addition, the binding affinity of BAPTA for polyvalent metals, is more selective than the IDA-like chelators. The dissociation constant of $Ca^{2+}$-BAPTA is reported to be 107 nM whereas the dissociation constant of $Mg^{2+}$-BAPTA is reported to be 17 mM. This approximately $10^6$ difference in affinity for $Ca^{2+}$ versus $Mg^{2+}$ permits, for instance, the selective removal or buffering of $Ca^{2+}$ in the presence of high concentrations of $Mg^{2+}$. The affinity of BAPTA-derived chelators can be slightly increased by addition of electron donating groups and decreased by addition of electron withdrawing groups (Tsien, supra; CELL CALCIUM 10, 491 (1989)).

Scientists have taken advantage of the selectivity and affinity of BAPTA to develop $Ca^{2+}$ ion selective fluorescent indicators that incorporate the basic BAPTA structure, including quin-2, fura-2 and indo-1 (U.S. Pat. No. 4,603,209 to Tsien, et al. (1986) ('209 patent); fluo-3 and rhod-2 (U.S. Pat. No. 5,049,673 to Tsien, et al. 1991) ('673 patent); and FURA RED™ (Molecular Probes, Inc., Eugene, Oreg., trademark for 1-[6-amino-2-(5-oxo-2-thioxo-4-thiazolidinylidene) methyl-5-benzofuranyloxy]-2-(2,2-amino-5'-methyl-phenoxy) ethane N,N, N', N'-tetraacetic acid and the tetra acetyloxymethyl ester thereof, U.S. Pat. No. 4,849,362 to DeMarinis, et al. (1989)). The structure of all these fluorescent indicators incorporates the aromatic BAPTA ring into a conjugated heterocyclic system through a trans-ethylenic bond which is either fixed (e.g. fura-2 and FURA RED) or rotating (e.g. fluo-3 and indo-1). Additional fluorescent indicators for $Ca^{2+}$ have been described by Tsien (*Intracellular Measurements of Ion Activities*, ANN. REV. BIOPHYS. BIOENG. 12, 91 (1983)), however these all have limitations in fluorescence response or other properties and do not involve the formation of reactive intermediates such as those described in this invention. All these ion selective indicators exhibit a change in optical properties upon binding $Ca^{2+}$ that can be used to determine changes in the levels of intracellular $Ca^{2+}$.

Although numerous publications have described the use of BAPTA derivatives as soluble indicators and buffers to either measure or control ion concentrations, BAPTA derivatives with one or two reactive groups used to attach the BAPTA derivative to a polymolecular assembly while preserving the high $Ca^{2+}$ affinity and $Ca^{2+}$ versus $Mg^{2+}$ selectivity of BAPTA have not previously been described. The '209 to Tsien, et al. discloses an amino-, aminomethyl-, and aminoethyl-aldehyde BAPTA intermediate used to synthesize fused heterocyclic aromatic indicators with a trans-ethylenic linkage between BAPTA and the fluorophore, but the '209 patent does not describe a reactive BAPTA derivative that can be used to conjugate BAPTA to a carrier and/or fluorophore with a linkage that contains more than one sigma bond in a row. The same linkage that allows for attachment of the chelator molecule to a wide range of polymolecular materials, also allows for attachment of the chelators to oxygen-containing heterocyclic fluorophores, to form novel and improved indicators.

Some of the indicator compounds formed in this way have an excitation wavelength that extends into the red range giving an emission well removed from any cellular background fluorescence and lowering light damage to cellular structures. The shorter wavelength light needed to excite fura-2 and indo-1 (340–360 nm) has been shown to damage cellular structures. The development of fluo-3 and rhod-2, with peak excitations wavelengths at 505 nm and 550 nm respectively, lowered UV induced cell damage and interference from cellular background fluorescence, but not as effectively as the most effective of the new compounds. Furthermore, the complex synthetic methods used to form the prior art indicators with the trans-ethylenic linkage limits the number of useful compounds that can be made in this way. The relatively easier conjugation of the reactive chelators of this invention increases the number of indicator compounds that can be made readily available.

SUMMARY OF THE INVENTION AND DESCRIPTION OF PREFERRED EMBODIMENTS

Figure 1:
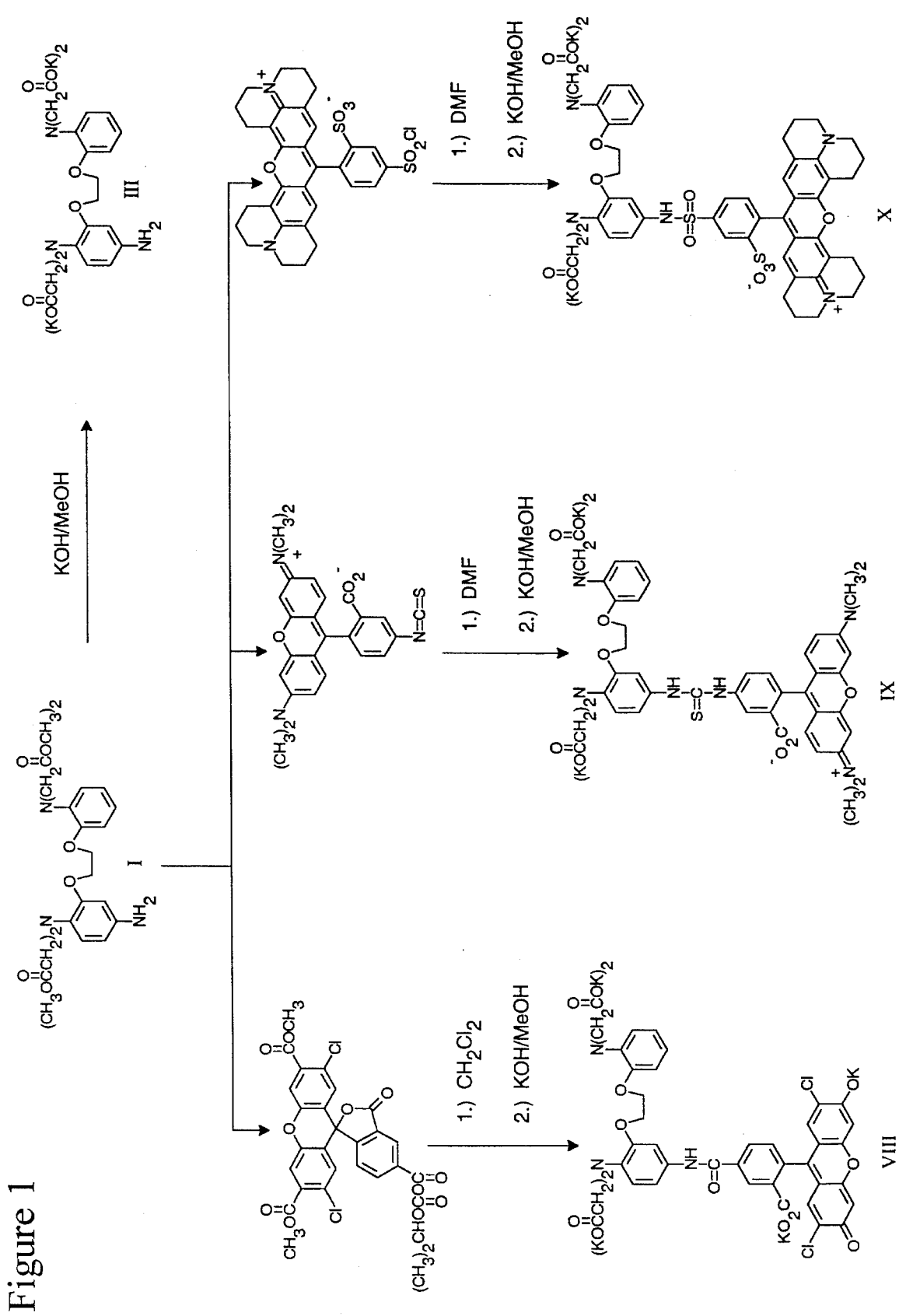
FIG. 1: Synthetic route to reactive derivatives and conjugates of 5-amino BAPTA
Figure 2:
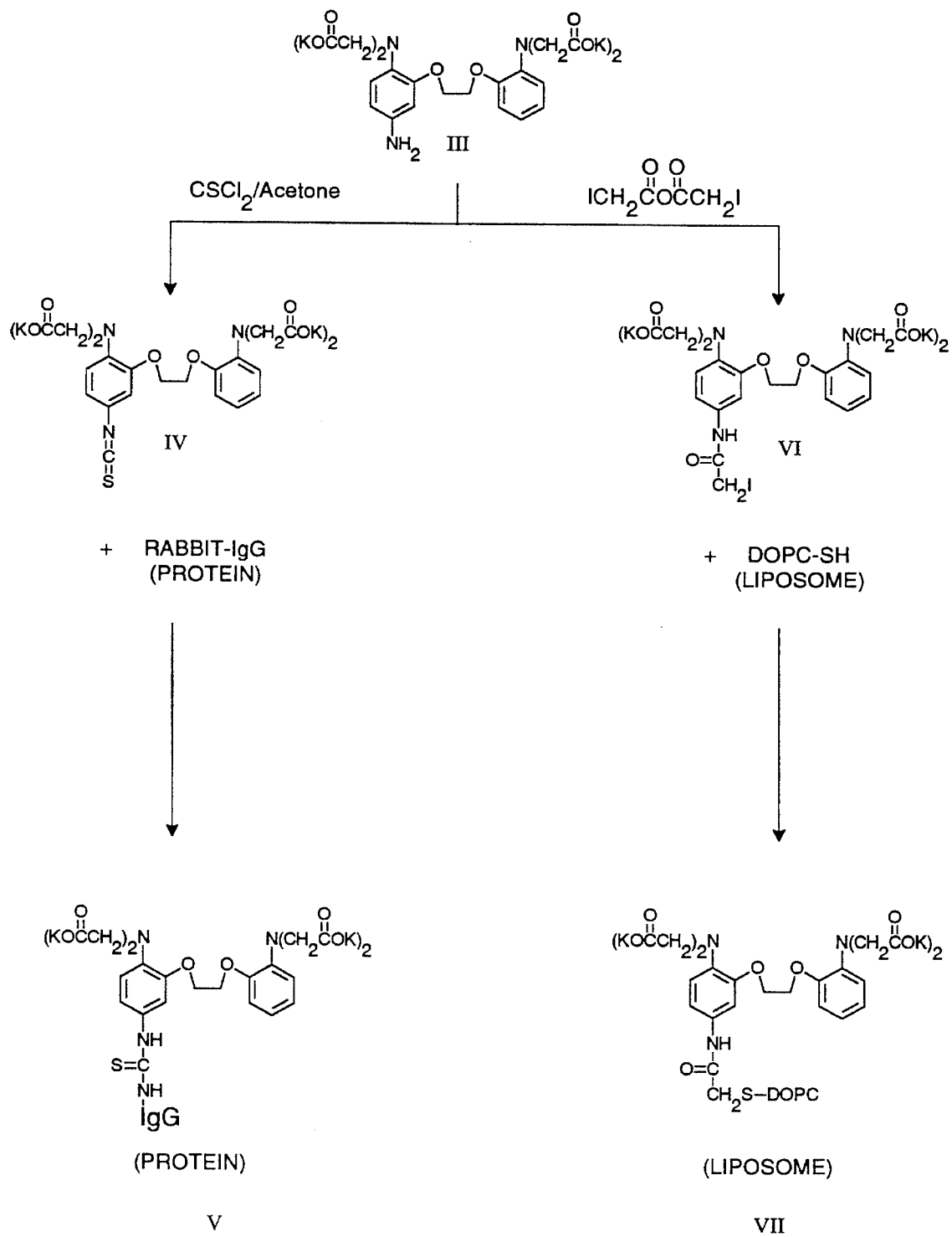
FIG. 2: Synthetic route to reactive derivatives and conjugates of 5-amino BAPTA
Figure 3:
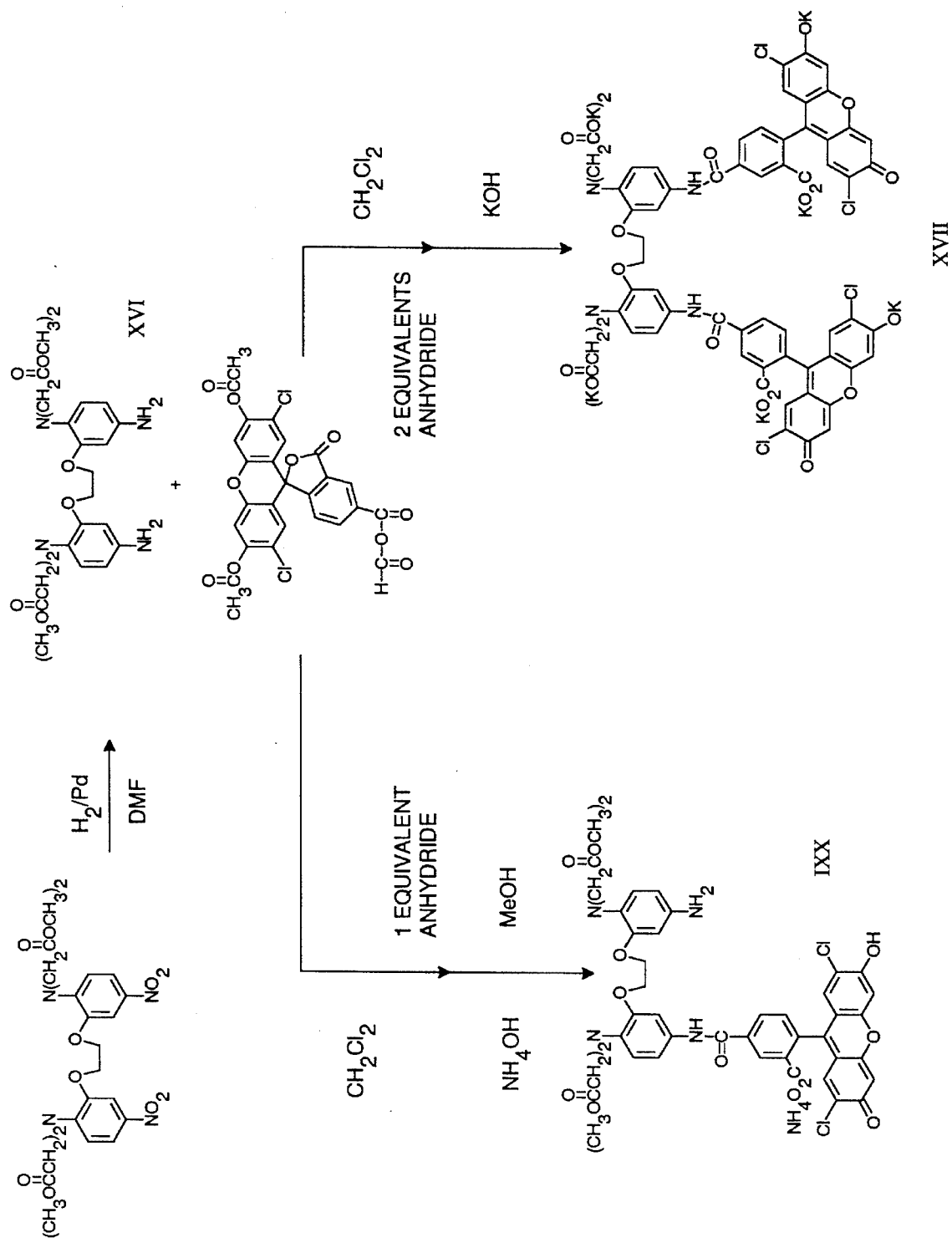
FIG. 3: Synthetic route to 5,5'-diamino BAPTA and conjugates of 5,5'-diamino BAPTA
Figure 4:
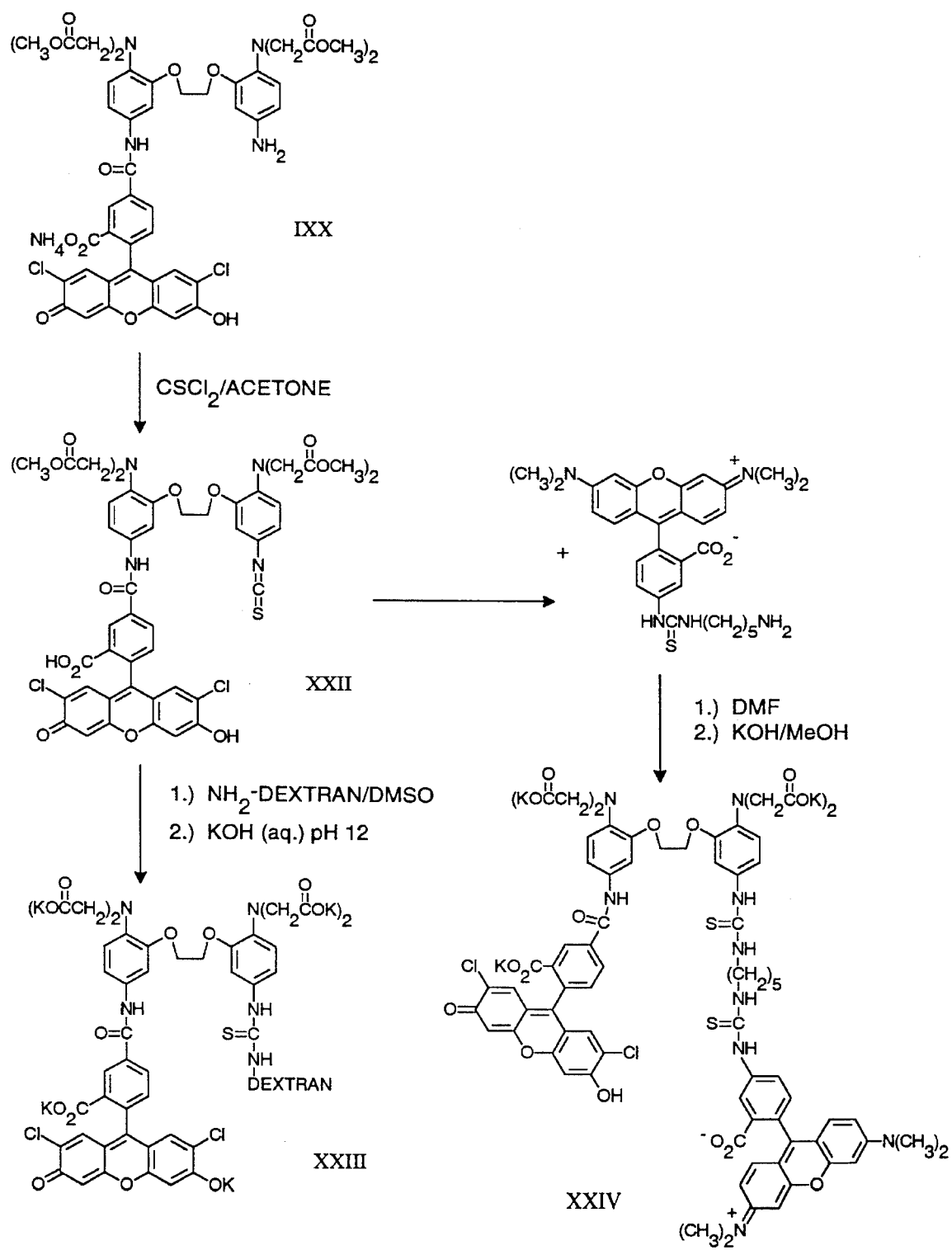
FIG. 4: Synthetic route to reactive derivatives and conjugates of 5,5'-diamino BAPTA
Figure 5:
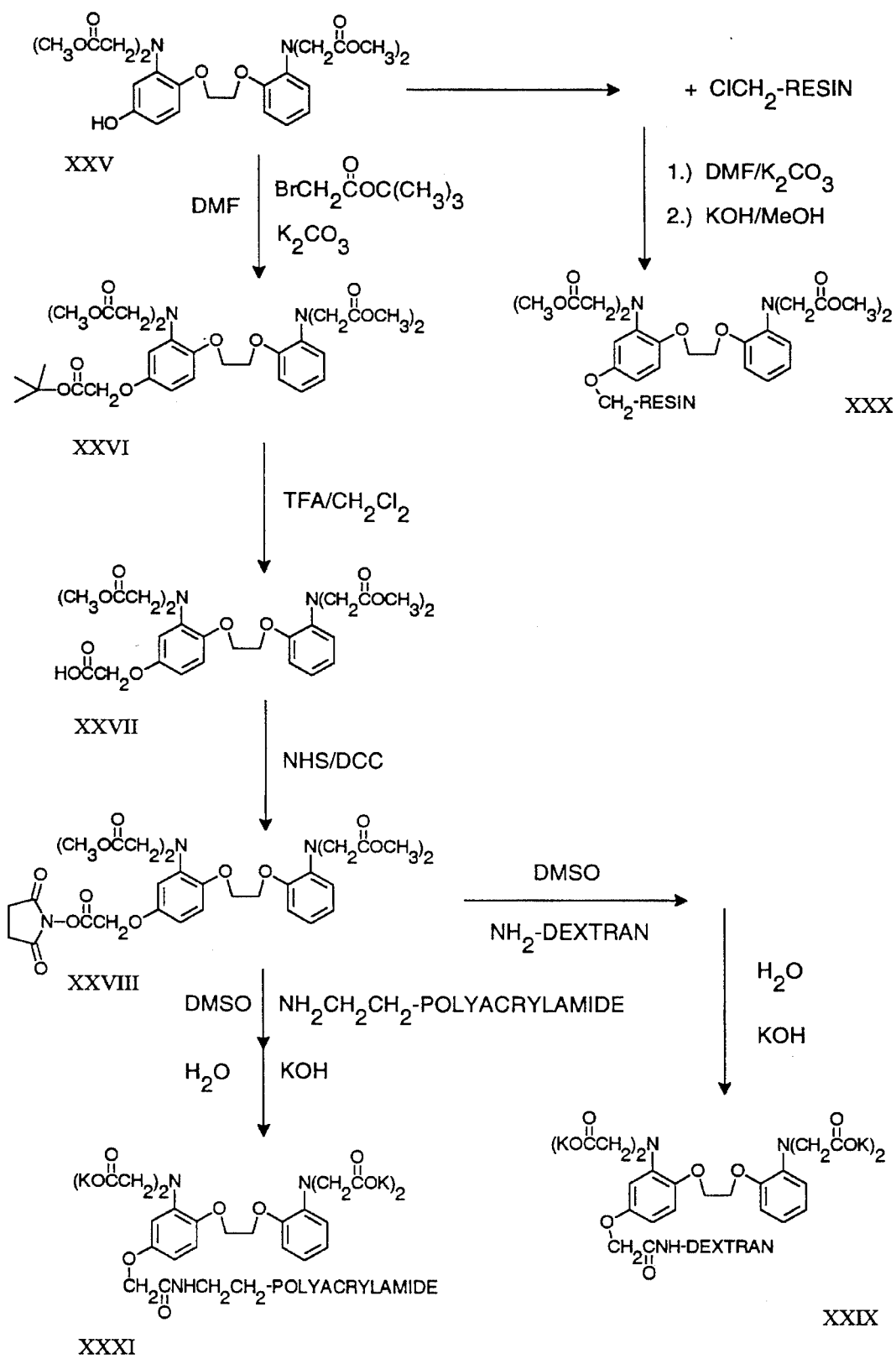
FIG. 5: Synthetic route to reactive derivatives and conjugates of 4-hydroxy BAPTA

The present invention is based on a chelator molecule derived from 1,2-bis-(2-aminophenoxyethane)-N,N,N',N'-tetraacetic acid (BAPTA) used to form novel fluorescent indicators and conjugates. The synthesis of novel conjugates and indicators have in common the use of a reactive BAPTA-like chelator molecule of the formula [Formula A]:

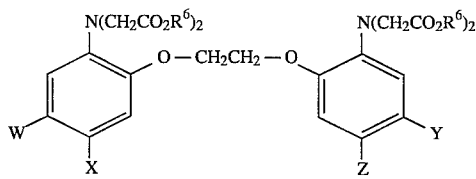

where at least one of W and X is a functional group. The functional group can be used to couple the chelator molecule to other synthetic or natural molecules, by reacting with an appropriate functional group on the molecule being coupled to form a covalent bond. Table 1 lists the functional groups which can be used to form the novel reactive BAPTA-like molecules and the groups with which they typically react. The tabulation is not all inclusive since with the appropriate choice of solvent, temperature and catalysts, other functional groups can be made to react. Alternative equivalent functional groups will be obvious to one skilled in the art.

TABLE 1

| FUNCTIONAL GROUPS | | |
|---|---|---|
| FUNCTIONAL GROUPS (attached to BAPTA) | REACT WITH: (on other molecules) (linkage) | TO YIELD: |
| alcohols/phenols | alkyl halides | ethers |
| haloacetamides maleimides alkyl halides alkyl sulfonates | thiols | thioethers |
| alkyl halides alkyl sulfonates | alcohols/phenols | ethers |
| thiols | haloacetamides maleimides | thioethers |
| amines/anilines | sulfonyl halides carboxylic acids anhydrides activated esters* | sulfonamides carboxamides |
| | alkyl halides isocyanates isothiocyanates | alkyl amines ureas thioureas |
| carboxylic acids anhydrides activated esters* | amines/anilines | carboxamides |
| isocyanates | amines/anilines | ureas |
| isothiocyanates | amines/anilines | thioureas |

*activated esters, as understood in the art, generally have the formula —COΩ, where Ω is a good leaving group (e.g. oxysuccinimidyl (—ONC$_4$H$_4$O$_2$), -1-oxybenzotriazolyl (—OC$_6$H$_4$N$_3$); or a phenoxy group or phenoxy substituted one or more times by electron withdrawing substituents such as nitro, fluoro, chloro, cyano, or trifluoromethyl, or combinations thereof, used to form activated phenyl esters; or a carboxylic acid activated by a carbodiimide to form an anhydride or mixed anhydride —OCOR$^8$ or —OCNR$^8$NHR$^9$, where R$^8$ and R$^9$, which may be the same or different, are C$_1$–C$_6$ alkyl, C$_1$–C$_6$ perfluoroalkyl, or C$_1$–C$_6$ alkoxy; or cyclohexyl, 3-dimethylaminopropyl, or N-morpholinoethyl).

One or both of Y and Z, and/or the other of W and X, may also be functional group(s), i.e. at least one and as many as four of the substituents W, X, Y, Z of Formula A are functional groups, all of which may be the same or different. The term functional group is not limited to a reactive terminus of the functional group that reacts to form a covalent bond with other molecules. The functional group optionally includes a spacer portion which links the reactive portion of the group to the aromatic core of the BAPTA-like molecule, according to the formula $(R^1)_n(R^2)$. When the spacer portion of the functional group ($R^1$) is absent (n=0), the reactive terminus of each functional group ($R^2$) is attached directly to the aromatic core of the BAPTA-like molecule by a covalent bond. When an alkyl spacer portion of the functional group is present (n=1), the spacer $R^1$ is —OCH$_2$R$^3$—, —SR$^3$—, —NHCOCH$_2$R$^3$—, —CONHCH$_2$R$^3$—, —NHSO$_2$R$^3$—, —NHCONHCH$_2$R$^3$—, or —NHCSNHCH$_2$R$^3$—, where R$^3$ is (CH$_2$)$_m$ and m=1–18. Where the functional group will be used to attach oxygen heterocycle fluorophores, as described in embodiments below, m is preferably less than 7. When an aryl spacer portion of the functional group is present (n=1), the spacer $R^1$ is typically —OR$^{3'}$—, —SR$^{3'}$—, —NHCOR$^{3'}$—, —CONHR$^{3'}$—, —NHSO$_2$R$^{3'}$—, —NHCONHR$^{3'}$—, or —NHCSNHR$^{3'}$—, where $R^{3'}$ is phenylene (—C$_6$H$_4$—). The reactive terminus of the functional group ($R^2$) is an alcohol or phenol, a thiol, a haloacetamide, an alkyl halide, an alkyl sulfonate, an amine or aniline, a carboxylic acid, an anhydride, an isocyanate, an isothiocyanate, an activated ester, or a maleimide

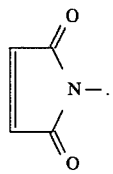

Preferably, R² is —NH₂, —NCO, —NCS, —SH, —OH, maleimidyl (—NC₄H₂O₂) linked through the nitrogen atom; an alkyl halide or alkyl sulfonate (—CH₂Q) or haloacetamide (NHCOCH₂Q), where Q is Cl, Br, I, methane sulfonyloxy, p-toluenesulfonyloxy, or trifluoromethanesulfonyloxy; or R² is —COR⁷ or —O(CH₂)COR⁷, where R⁷ is Cl, —OH, oxysuccinimidyl (—ONC₄H₄O₂), -1-oxybenzotriazolyl (—OC₆H₄N₃); or a phenoxy or a phenoxy substituted one or more times by substituents that are nitro, fluoro, chloro, cyano, or trifluoromethyl, or combinations thereof; or R² is OCNR⁸NHR⁹, or where R⁸ and R⁹, which may be the same or different, are C₁-C₆ alkyl, perfluoroalkyl, or alkoxy; or cyclohexyl, 3-dimethylaminopropyl, or N-morpholinoethyl. More preferably, at least one functional group terminates in an amine or an aniline, an alcohol or a phenol, an isothiocyanate, an anhydride, or a succinimidyl ester. Preferably, functional groups at the 5 or 5' position of the chelator molecule are used for the attachment of aromatic oxygen heterocyclic fluorophores described below.

The substituents W, X, Y, and Z of Formula A that are not functional groups (with or without spacers) are optionally H, CH₃, NO₂, CF₃, F, Cl, Br, I, or —OR⁵, —CO₂R⁵, or —OCH₂CO₂R⁵, where R⁵ is an alkyl group with about 1–5 carbons, a benzyl (C₆H₅CH₂—), or an alpha-acyloxyalkyl or other pharmaceutically acceptable esterifying group, or a pharmaceutically acceptable salt; or combinations thereof. As used herein pharmaceutically acceptable salt means non-toxic salts of carboxylic acids known and used in the pharmaceutical industry, such as K, Na⁺, Cs⁺, Li⁺, Ca²⁺, Mg²⁺, NR₄⁺ where R=H or C₁-C₄ alkyl, or combinations thereof, or combinations of acid salts of these counterions plus free acid groups. Pharmaceutically acceptable esterifying groups are those that form readily hydrolyzable esters which are known and used in the pharmaceutical industry, such as alpha-acyloxyalkyl esters, especially acetoxymethyl (CH₃CO₂CH₂—) esters. The incorporation of such non-functional-group substituents can be used to enhance the affinity of the ion-selective molecule for polycations (such as the lower alkyl groups, methyl and ethyl) or lessen the affinity (such as carboxylic acid derivatives, nitro, cyano, trifluoromethyl and halogens such as chlorine, bromine and iodine). These substituents can also be added after the reactive BAPTA-like molecule is incorporated into other materials as described below.

In combination with or alternative to the non-functional group substituents already described above, any substituent W, X, Y, or Z of Formula A that is not a functional group may be a 2-indolyl fluorophore. Because of ease of synthesis, the indole is preferably located only at the 5 or 5' positions of the BAPTA-like molecule. The indole may be further substituted by a carboxy group according to the formula —CO₂R⁵, where R⁵ is an alkyl group with about 1–5 carbons, a benzyl (C₆H₅CH₂—), or an alpha-acyloxyalkyl or other pharmaceutically acceptable esterifying group, or a pharmaceutically acceptable salt. Alternatively, where Y and Z are not functional groups, Y taken together with Z and the aromatic carbons at the 4' and 5' positions of Formula A can form a benzofuran or substituted benzofuran fluorophore. The benzofuran fluorophore may be substituted by a heteroaryl group (i.e. an aromatic heterocycle that contains at least one heteroatom (non-carbon atom) forming the ring structure, such as an oxazolyl), which may be further substituted by a carboxy group, according to the formula —CO₂R⁵, where R⁵ is an alkyl group with about 1–5 carbons, a benzyl (C₆H₅CH₂—), or an alpha-acyloxyalkyl or other pharmaceutically acceptable esterifying group, or a pharmaceutically acceptable salt.

The chelator portion of the molecule (—N(CH₂CO₂R⁶)₂ in Formula A), includes both a "pre-chelator" form of the molecule in which the chelator portion is protected (where R⁶ is an alkyl group with about 1–5 carbons, a benzyl, or an alpha-acyloxyalkyl or other pharmaceutically acceptable esterifying group), as well as an active chelator form of the molecule in which the four chelating carboxylic acids are deprotected (R⁶ is a pharmaceutically acceptable salt). The chelating carboxylic acids may be deprotected before or after the addition of the materials described below. Such protection may be required for certain uses of the indicating chelator, for example the acetoxymethyl esters can be used to facilitate entry of the chelating indicators into living cells.

The reactive BAPTA-like molecules are formed by a variety of synthetic schemes, depending on the position and composition of the various functional group substituents. The reactive BAPTA-like molecules may be non-fluorescent but allow for the covalent attachment of fluorophores through conjugation with one or more of the functional groups; or one or more fluorophores may be incorporated into the reactive BAPTA-like molecule during synthesis as a benzofuran or indolyl. The following embodiments are exemplified in greater detail below: functional group at W (Example 25); functional group at X (Examples 3, 4); functional groups at X and Z (Example 15); functional group at X, and Y and Z taken together form a benzofuran (Examples 32, 33); functional group at W, carboxy-substituted 2-indolyl at X (Example 29). In addition, embodiments with functional groups at W and X can be synthesized by nitration of the 5'-methyl version of compound XXVII at the 5 position, followed by reduction to the amine to give 5-amino-4-carbomethoxy BAPTA-tetramethyl ester; in the same way, functional groups at W and Z can be synthesized beginning with the 5-methyl version of Compound XXVII; functional groups at W,X and Z can be synthesized by di-nitration of Compound XXVII followed by reduction to the 4-carbomethoxy-5,5'-diamino BAPTA; functional groups at W and Y can be synthesized by analogy to Compound XXVII by starting the synthesis with the corresponding 4,4'-dihydroxy BAPTA and proceeding as in Example 29; an example of an embodiment with a functional group at W, and Y and Z taken together to form a benzofuran can be made from 4-carbomethoxy-5-methyl BAPTA where Y and Z taken together form a benzofuran; functional group at W carboxy substituted 2-indolyl at Z is synthesized by analogy to Compound XXXVI starting with a 4-carbomethoxy-5-methyl-5'-formyl BAPTA tetraester; in the same way, a BAPTA with a functional group at W and a carboxy substituted 2-indolyl at X and Z can be made from the 4-carbomethoxy-5,5' diformyl BAPTA; functional group at W with an enhancer/modifier at X,Y or Z can be synthesized, for example, by bromination at the 5, 5' or both positions of compound XXVII.

The reactive BAPTA-like chelator molecule can be linked by covalent bonds to a variety of materials in such a way that all four carboxylic acids of the BAPTA-like molecule remain available for chelation of metals. The affinity and selectivity for $Ca^{2+}$ and certain other polycations is highly retained ($K_d$ for $Ca^{2+}<10^{-5}M$), while the affinity for $Mg^{2+}$ and certain other small polycations and for monocations is relatively low ($K_d$ for $Mg^{2+}>10^{-3}M$). Preferably, the covalent linkage is an ether, a thioether, a carboxamide, a sulfonamide, a urea or a thiourea linkage, formed according to one of the conjugation reactions described in Table 1, or equivalent linkages that are particularly resistant to hydrolysis.

Fluorescent Chelators With a Carrier

In one embodiment of the invention, a fluorescent derivative of reactive BAPTA-like molecule is immobilized on a carrier by using one of the functional groups of the reactive molecule to form a linkage with a polymolecular assembly that is an ether, a thioether, a carboxamide, a sulfonamide, an alkyl amide, a urea or a thiourea linkage, according to one of the conjugation reactions described in Table 1. The conjugation yields a fluorescent ion-selective conjugate with a carrier according to the formula [Formula B]:

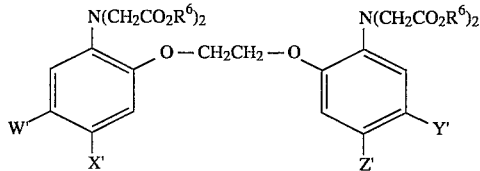

where at least one of the substituents W' and X' contains a biologically compatible polymolecular assembly (-POLY) covalently linked to the BAPTA-like molecule. The polymolecular assembly can be covalently linked to the core BAPTA-like molecule using functional groups optionally with or without spacers according to the formula $(R^a)_n(R^b)$-POLY. When the spacer is absent, n=0. When present (n=1), the spacer $R^a$ is —OCH$_2$R$^3$—, —OR$^{3'}$—, —SR$^3$—, —SR$^{3'}$—, —NHCOCH$_2$R$^3$—, —NHCOR$^{3'}$—, —CONHCH$_2$R$^3$—, —CONHR$^{3'}$—, —NHSO$_2$R$^3$—, —NHSO$_2$R$^{3'}$—, —NHCONHCH$_2$R$^3$—, —NHCONHR$^{3'}$—, —NHCSNHCH$_2$R$^3$—, or —NHCSNHR$^{3'}$—, where $R^3$ is (CH$_2$)$_m$ and m= 1–18, and $R^{3'}$ is phenylene (—C$_6$H$_4$—). The polymolecular assembly attaches covalently to the reactive portion of the functional group such that $R^b$ is —NH—, —NHCO—, —NHCS, —S—, —O—, —CO—; or —CH$_2$— or —COCH$_2$—, or succinimidyl

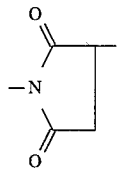

A wide variety of natural and synthetic polymolecular assemblies are suitable for use in this embodiment of the invention. As used herein, polymolecular assembly means a high molecular weight material made up of repeating units of relatively smaller molecules linked together to form a discrete compound. The repeating units may be linked covalently, as in polystyrene or polysaccharides, or may be linked non-covalently as in liposomes and micelles, or may be linked by a combination of covalent bonds and non-covalent attractions as in polypeptides and oligonucleotides with significant degrees of secondary and tertiary structure. A suitable polymolecular assembly is a biologically compatible material having an average molecular weight of greater than about 750 Daltons, preferably from about 1000 to about 10,000,000 Daltons, more preferably from about 1000 to about 500,000 Daltons. The molecular weight of such materials is almost always polydisperse. As used herein, biologically compatible materials are materials with a low intrinsic interaction of the polymer with biological materials. Suitable polymolecular assemblies may be soluble in water or organic solvents or may be insoluble or may be rendered insoluble, such as by having cross-linking groups.

Suitable polymolecular assemblies include but are not limited to synthetic polymeric resins and gels such as polystyrene and polyacrylic acids, amides, and esters; glass; polyols such as polyvinyl alcohol and polysaccharides such as agarose, cellulose, dextrans, ficols, heparin, glycogen, amylopectin, mannan, inulin, and starch; polypeptides and proteins; and oligonucleotides and nucleic acids; and also include naturally and chemically cross-linked forms thereof. Preferred water soluble polymolecular assemblies are dextrans, water soluble proteins (especially antibodies), nucleic acids (particularly DNA, RNA and synthetic oligonucleotides), and polyacrylic acids, amides and esters. Preferred water insoluble polymolecular assemblies are polymeric materials such as agarose and polystyrene, glass, and natural and synthetic liposomes.

Preferably the polymolecular assembly possesses one or more reactive sites such as amines, alcohols (including phenols) and thiols, that readily react with the functional group(s) on the reactive BAPTA-like molecule. Natural or synthetic polymolecular assemblies that do not inherently possess reactive sites that readily react with the functional group on the BAPTA-like molecule (see Table 1), may be modified, by methods well known and documented in the art, to add reactive sites with which the functional groups of the BAPTA-like molecule will readily form covalent bonds. Numerous suitable polymers or modified polymers are commercially available from suppliers such as Bio-Rad and Pharmacia.

In addition to the polymolecular assembly, the fluorescent ion-selective conjugate of Formula B also contains at least one fluorophore. The fluorophore may be included as part of the reactive molecule of Formula A used to synthesize the fluorescent, ion-selective polymolecular assembly. Alternatively, the fluorophore may be linked to the BAPTA-like molecule through reaction with one of the functional groups. At least one of substituents X' and Z' of Formula B contains a fluorophore according to the formula $(R^a)_n(R^b)_n$-FLUOR, or Z' taken together with Y' and the aromatic carbons at the 4' and 5' positions form a benzofuran or heteroaryl- or carboxyheteroaryl-substituted benzofuran fluorophore.

Where Z' taken together with Y' and the aromatic carbons at the 4' and 5' positions of Formula B form a benzofuran or substituted benzofuran fluorophore, the benzofuran fluorophore is incorporated into the reactive BAPTA-like molecule (Formula A) during synthesis of the reactive indicator (see, e.g., Example 33). The polymolecular assembly is then conjugated to the reactive indicator.

Where one of substituents X' and Z' of Formula B contains a fluorophore, the fluorophore is covalently attached to the BAPTA-like molecule according to the formula $(R^a)_n(R^b)_n$-FLUOR, where -FLUOR is an aromatic oxygen heterocycle fluorophore, or is a 2-indolyl or carboxy substituted 2-indolyl fluorophore. The term aromatic oxygen heterocycle fluorophore, as used herein, means those fluorescent or fluorogenic aromatic compounds containing at least one oxygen heteroatom in the ring structure. Preferred oxygen heterocycle fluorophores are fluoresceins, rhodamines, and coumarins; including naphthofluoresceins, semi-naphthofluoresceins, rhodols, eosins, erythrosins, tetrachlorofluoresceins, dihydrofluoresceins, tetramethylrhodamines, rhodamines -B, -6G, -101, -110, -123, and -X, sulforhodamine 101 sulfonyl chlorides (Texas Red™), rosamines, hydroxy coumarins, alkoxy coumarins, dialkylaminocoumarins, trifluoromethyl coumarins; as well as conjugated reactive derivatives of fluoresceins, rhodamines, and coumarins used to form the linkages of Table 1.

When -FLUOR is a 2-indolyl or carboxy substituted 2-indolyl fluorophore, the indolyl fluorophore is incorporated into the reactive BAPTA-like molecule of Formula A during synthesis (Example 29) before attachment of the reactive indicator to the polymolecular assembly and there is no spacer or functional group used (n and n' are 0). When -FLUOR is an oxygen heterocycle, the fluorophores can be attached before or after the polymolecular assembly, optionally using functional groups with or without spacers. When the spacer is absent, n=0. When present (n=1), the spacer $R^a$ is —$OCH_2R^3$—, —$OR^{3'}$—, —$SR^3$—, —$SR^{3'}$—, —$NHCOCH_2R^3$—, —$NHCOR^{3'}$—, —$CONHCH_2R^3$—, —$CONHR^{3'}$—, —$NHSO_2R^3$—, —$NHSO_2^{R3'}$—, —$NHCONHCH_2R^3$—, —$NHCONHR^{3'}$—, —$NHCSNHCH_2R^3$—, or —$NHCSNHR^{3'}$—, where $R^3$ is $(CH_2)_m$ and m=1–6, and $R^{3'}$ is phenylene (—$C_6H_4$—), The fluorophore attaches covalently to the reactive portion of the functional group such that $R^b$ is —NH—, —NHCO—, —NHCS, —S—, —O—, —CO—; or —$CH_2$— or —$COCH_2$—, or succinimidyl.

The remainder of substituents W', X', Y', and Z', which may be the same or different, may contain additional fluorophores, according to the $(R^a)_n(R^b)_n$-FLUOR, or additional polymolecular assemblies according to the formula $(R^a)_n(R^b)_n$-POLY, in any of their described variations. In combination with or alternative to additional polymolecular assemblies or fluorophores, the remaining substituents may be independently H, $CH_3$, $NO_2$, $CF_3$, F, Cl, Br, I, —$OR^5$, —$CO_2R^5$, or —$OCH_2CO_2R^5$, where $R^5$ is an alkyl group with about 1–5 carbons, a benzyl ($C_6H_5CH_2$—), or a pharmaceutically acceptable esterifying group, or a pharmaceutically acceptable salt; or combinations thereof. As previously mentioned, the incorporation of such substituents can be used to enhance the affinity of the ion-selective molecule for polycations (such as the lower alkyl groups, methyl and ethyl) or lessen the affinity (such as carboxylic acid derivatives, nitro, cyano, trifluoromethyl and halogens such as chlorine, bromine and iodine).

As with the reactive intermediate described above, the chelator portion of the molecule (—$N(CH_2CO_2R^6)_2$ in both Formula A & B), includes both a "pre-chelator" form of the molecule in which the chelator portion is protected (where $R^6$ is an alkyl group with about 1–5 carbons, a benzyl, or an alpha-acyloxyalkyl or other pharmaceutically acceptable esterifying group), as well as an active chelator form of the molecule in which the four chelating carboxylic acids are deprotected ($R^6$ is a pharmaceutically acceptable salt). To facilitate preparation of the ion-selective chelators immobilized on a carrier, the chelating carboxylic acids of the reactive BAPTA-like molecule can be temporarily blocked such as by formation of esters that are removed either before or after formation of the ion-selective conjugate. In use, $R^6$ is almost exclusively a pharmaceutically acceptable salt.

The insoluble polymolecular assemblies are particularly useful for selective removal of ions from solution and from proteins that are brought into contact with the ion-selective conjugates (e.g. Examples 42, 43), whereas the water soluble conjugates can buffer or selectively transport ions in solutions including inside biological cells (e.g. Example 44). These ion-selective conjugates can also be used to selectively bind fluorescent or radioactive metals, often with very high affinity (e.g. Example 40). The general membrane impermeability of the soluble ion-selective conjugates permits their use to remove extracellular ions from cells without effecting intracellular ionic composition. Through appropriate selection of sizes of carriers or polymolecular assemblies, soluble BAPTA conjugates can be prepared that will either pass or will not pass through pores in membranes.

TABLE 2

| Properties of representative water soluble fluorescent chelators with carrier | | | | | | |
|---|---|---|---|---|---|---|
| Compound | | $K_dCa^{2+}(nM)^{1,2}$ | $Ex^3$ | $Em(+Ca^{2+})^4$ | Ex | $Em(-Ca^{2+})$ | D.O.S.$^5$ |
| XLIV | 10K MW | 346 | 341 | 495 | 367 | 501 | 1.0 |
|  | 70K MW | 436 | 341 | 496 | 364 | 503 | 9.3 |
| XXXVII | 10K MW | 251 | 342 | 408 | 356 | 466 | 0.6 |
|  | 70K MW | 363 | 343 | 408 | 360 | 464 | 3.0 |
| XXIII | 10K MW | 251 | 505 | 532 | 506 | 531 | 1.3 |
|  | 70K MW | 336 | 506 | 532 | 506 | 531 | 7.5 |

$^1$Dissociation constant for $Ca^{2+}$ determined according to Example 44
$^2$nM = nanomolar
$^3$Excitation wavelength (unit = nanometer)
$^4$Emission wavelength
$^5$Degree of Substitution (units = dyes/dextran) determined according to Example 45

Fluorescent Chelators Without a Carrier

In another embodiment of the invention, the reactive BAPTA-like molecule is attached to one or more fluorophores by using one of the functional groups of the reactive molecule to form a linkage with the fluorophore that is an ether, a thioether, a carboxamide, a sulfonamide, an alkyl amide, a urea or a thiourea linkage, according to one of the conjugation reactions described in Table 1. The conjugation yields a fluorescent ion-selective conjugate without a carrier according to the formula [Formula C]:

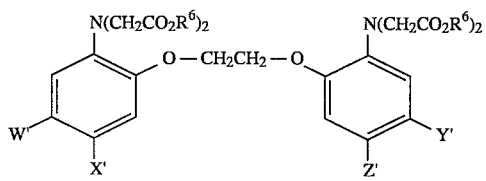

which is similar to Formula B above. Unlike Formula B, however, the compounds of Formula C contain no polymolecular assembly and at least one of W', X', Y' and Z' contains an aromatic oxygen heterocycle fluorophore. The oxygen heterocyclic fluorophore can be attached to the core BAPTA-like molecule using functional groups optionally with or without spacers according to the formula $(R^a)_n(R^b)$-FLUOR'. When the spacer is absent, n=0. When present (n=1), the spacer $R^a$ is —$OCH_2R^3$—, —$OR^{3'}$—, —$SR^3$—, —$SR^{3'}$—, —$NHCOCH_2R^3$—, —$NHCOR^{3'}$—, —$CONHCH_2R^3$—, —$CONHR^{3'}$—, —$NHSO_2R^3$—, —$NHSO_2R^{3'}$—, —$NHCONHCH_2R^3$—, —$NHCONHR^{3'}$—, —$NHCSNHCH_2R^3$—, or —$NHCSNHR^{3'}$—, where $R^3$ is $(CH_2)_m$ and m=1–6, and $R^{3'}$ is phenylene (—$C_6H_4$—). The fluorophore (-FLUOR') is an aromatic oxygen heterocycle, preferably fluorescein, rhodamine, or coumarin, or modified or conjugated reactive derivatives thereof, as described above. The oxygen heterocycle fluorophore attaches covalently to the reactive portion of the functional group such that $R^b$ is —NH—, —NHCO—, —NHCS, —S—, —O—, —CO—; or —$CH_2$— or —$COCH_2$—, or succinimidyl.

For the conjugates of Formula C, similarly to the conjugates of Formula B, the remainder of substituents W', X', Y', and Z', which may be the same or different, are independently H, $CH_3$ $NO_2$, $CF_3$, F, Cl, Br, I, —$OR^5$, —$CO_2R^5$, or —$OCH_2CO_2R^5$, where $R^5$ is an alkyl group with about 1–5 carbons, a benzyl ($C_6H_5CH_2$—), an alpha-acyloxyalkyl or other pharmaceutically acceptable esterifying group, or a pharmaceutically acceptable salt; or combinations thereof. The remaining substituents may additionally or alternatively contain one or more fluorophores according to the formula $(R^a)_n(R^b)_{n'}$-FLUOR, or Z' taken together with Y' and the aromatic carbons at the 4' and 5' positions form a benzofuran or substituted benzofuran fluorophore.

Where a remaining substituent contains a fluorophore covalently attached to the BAPTA-like molecule according to the formula $(R^a)_n(R^b)_{n'}$-FLUOR, -FLUOR is an aromatic oxygen heterocycle, preferably fluorescein, rhodamine, or coumarin, or modified or conjugated reactive derivatives thereof, as described above, or FLUOR is a 2-indolyl or carboxy substituted 2-indolyl fluorophore, and n and n'=0 or 1. When -FLUOR is a substituted or unsubstituted 2-indolyl fluorophore, the fluorophore is incorporated into the reactive BAPTA-like molecule of Formula A during synthesis and there is no spacer or functional group used (n and n' are 0). When -FLUOR' is an oxygen heterocycle, the fluorophores can be covalently attached optionally using functional groups with or without spacers. When the spacer is absent, n=0. When present (n=1), the spacer $R^a$ is —$OCH_2R^3$—, —$OR^{3'}$—, —$SR^3$—, —$SR^{3'}$—, —$NHCOCH_2R^3$—, —$NHCOR^{3'}$—, —$CONHCH_2R^3$—, —$CONHR^{3'}$—, —$NHSO_2R^3$—, —$NHSO_2R^{3'}$—, —$NHCONHCH_2R^3$—, —$NHCONHR^{3'}$—, —$NHCSNHCH_2R^3$—, or —$NHCSNHR^{3'}$—, where $R^3$ is $(CH_2)_m$ and m=1–6, and $R^{3'}$ is phenylene (—$C_6H_4$—). The oxygen heterocycle fluorophore attaches covalently to the reactive portion of the functional group such that $R^b$ is —NH—, —NHCO—, —NHCS, —S—, —O—, —CO—; or —$CH_2$or —$CH_2$— or —$COCH_2$—, or succinimidyl (n'=1).

As with the compounds of Formula A and B, $R^6$ is an alkyl group with about 1–5 carbons, a benzyl, an alpha-acyloxyalkyl or other pharmaceutically acceptable esterifying group, or a pharmaceutically acceptable salt.

The fluorescent ion-selective conjugates (indicators) of Formula C exhibit an increase in fluorescence emission on reversibly binding a single calcium ion. These indicators are used to measure $Ca^{2+}$ levels in solutions, in single cells and in suspensions of cells. The increase in emission intensity of the dye is monitored as the concentration of $Ca^{2+}$ increases to give a calibration curve according to Example 38. When the dye is loaded into cells, the emission intensity of the intracellular dye is compared to the calibration curve to determine intracellular free $Ca^{2+}$ concentration.

To measure free $Ca^{2+}$ levels in a single cell, one must be able to achieve a strong emission signal from a small amount of dye. The signal that can be generated from a single dye molecule depends on the amount of light the molecule will absorb (extinction coefficient) and the portion of that light re-emitted as a fluorescent emission (quantum yield). These two factors, when multiplied together, give an idea of the relative fluorescence intensity. As the intensity is improved, the amount of dye necessary to achieve a meaningful signal is scaled back proportionately. The subject indicators have an improved quantum yield relative to other indicators in common use, resulting in a greater relative intensity. In particular, Compound VIII is five times more fluorescent than the spectrally similar fluo-3 (U.S. Pat. No. 5,049,673 to Tsien, et al. (1991)) and Compound IX is two times as fluorescent as rhod-3 ('673 patent). Tsien, et al. do not describe compounds with spectra similar to Compounds X or XI. The novel indicators also photobleach at a significantly slower rate, which may permit their use over longer periods of illumination.

TABLE 3

Properties of fluorescent conjugates of 5-amino BAPTA

| | | Ex | | Em | |
|---|---|---|---|---|---|
| Compound | KdCa$^{2+}$* | High Ca$^{2+}$ | Low Ca$^{2+}$ | High Ca$^{2+}$ | Low Ca$^{2+}$ |
| VIII | 189 nM | 506 | 506 | 534 | 533 |
| IX | 328 nM | 555 | 554 | 576 | 575 |
| X | 205 nM | 588 | 587 | 610 | 610 |
| XVII | 450 nM | 506 | 506 | 534 | 533 |

| | QY[1] | | |
|---|---|---|---|
| Indicator | High Ca$^{2+}$ | Low Ca$^{2+}$ | Em Increase[2] |
| VIII | 0.75 | 0.06 | 13x |
| IX | 0.33 | 0.11 | 3x |
| X | 0.53 | 0.18 | 3x |
| XVII | n.d. | n.d. | 60x | n.d. = not determined
*Dissociation constant of Ca$^{2+}$ determined according to Example 38.
[1]Quantum Yield in high/low Ca$^{2+}$ buffers from Example 38.
[2]Increase in emission intensity In addition, unlike the $Ca^{2+}$ indicators currently in widespread use, for which complex synthetic methods limit the number of useful compounds that can be made, these compounds represent a flexible new method for the design and synthesis of fluorescent ion indicators.

Non-Fluorescent Chelators With a Carrier

In yet another embodiment of the invention, a non-fluorescent derivative of reactive BAPTA-like molecule is immobilized on a solid support or carrier by using one of the functional groups of the reactive molecule to form a linkage with a polymolecular assembly that is an ether, a thioether, a carboxamide, a sulfonamide, an alkyl amide, a urea or a thiourea linkage, according to one of the conjugation reactions described in Table 1. The conjugation yields a non-fluorescent ion-selective conjugate according to the formula [Formula D]:

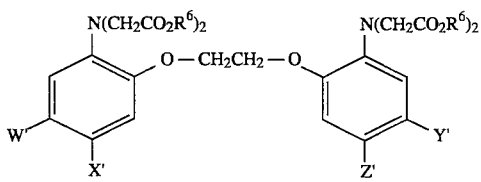

which is similar to Formula B above. Unlike Formula B, however, the compounds of Formula D contain no fluorophore and at least one of W', X', Y' and Z' contains a biologically compatible polymolecular assembly (-POLY) covalently linked to the BAPTA-like molecule. As with the conjugates of Formula B, the polymolecular assembly can be covalently linked to the core BAPTA-like molecule using functional groups optionally with and/or without spacers according to the formula $(R^a)_n(R^b)$-POLY. When the spacer is absent, n=0. When present (n=1), the spacer $R^a$ is —OCH$_2$R$^3$—, —OR$^{3'}$—, —SR$^3$—, —SR$^{3'}$—, —NHCOCH$_2$R$^3$—, —NHCOR$^{3'}$—, —CONHCH$_2$R$^3$—, —CONHR$^{3'}$—, —NHSO$_2$R$^3$—, —NHSO$_2$R$^{3'}$—, —NHCONHCH$_2$R$^3$—, —NHCONHR$^{3'}$—, —NHCSNHCH$_2$R$^3$—, or —NHCSNHR$^{3'}$, where R$^3$ is (CH$_2$)$_m$ and m=1–18, and R$^{3'}$ is phenylene (—C$_6$H$_4$—). The polymolecular assembly naturally attaches covalently to the reactive portion of the functional group such that $R^b$ is —NH—, —NHCO—, —NHCS, —S—, —O—, —CO—; or —CH$_2$— or —COCH$_2$—, or succinimidyl.

As with the fluorescent conjugates of Formula B, a wide variety of natural and synthetic polymolecular assemblies are suitable for use in this embodiment. A suitable polymolecular assembly is a biologically compatible material having an average molecular weight of greater than about 750 Daltons, preferably from about 1000 to about 10,000,000 Daltons. Suitable polymolecular assemblies may be soluble in water or organic solvents or may be insoluble or may be rendered insoluble, such as by having cross-linking groups.

Suitable polymolecular assemblies include but are not limited to synthetic polymeric resins and gels such as polystyrene and polyacrylic acids, amides, and esters; glass; polyols such as polyvinyl alcohol and polysaccharides such as agarose, cellulose, dextrans, ficols, heparin, glycogen, amylopectin, mannan, inulin, and starch; polypeptides and proteins; and oligonucleotides and nucleic acids. Preferred water soluble polymolecular assemblies are natural and synthetic dextrans, water soluble proteins (especially antibodies), nucleic acids (particularly DNA, RNA and synthetic oligonucleotides), and polyacrylic acids, amides and esters. Preferred water insoluble polymolecular assemblies are polymeric materials such as agarose and polystyrene, glass, and natural and synthetic liposomes.

Preferably the polymolecular assembly possesses one or more reactive sites such as amines, alcohols (including phenols) and thiols, that readily react with the functional group(s) on the reactive BAPTA-like molecule. Natural or synthetic polymolecular assemblies that do not inherently possess reactive sites that readily react with the functional group on the BAPTA-like molecule (see Table 1), may be modified, by methods well known and documented in the art, to add reactive sites with which the functional groups of the BAPTA-like molecule will readily form covalent bonds. Numerous suitable polymers or modified polymers are commercially available.

The remainder of substituents W', X', Y', and Z', which may be the same or different, are optionally H, CH$_3$, NO2, CF$_3$, F, Cl, Br, I, —OR$^5$, —CO$_2$R$^5$, or —OCH$_2$CO$_2$R$^5$, where R$^5$ is an alkyl group with about 1–5 carbons, a benzyl (C$_6$H$_5$CH$_2$—), an alpha-acyloxyalkyl or other pharmaceutically acceptable esterifying group, or a pharmaceutically acceptable salt, or one or more additional polymolecular assemblies according to the formula $(R^a)_n(R^b)$-POLY, in any of its described variations; or combinations thereof.

As with the compounds of Formula A, B and C, R$^6$ is an alkyl group with about 1–5 carbons, a benzyl, an alpha-acyloxyalkyl, or other pharmaceutically acceptable esterifying group, or a pharmaceutically acceptable salt.

The following examples are representative of different embodiments of the invention. Specific properties are intended to be illustrative of the range of possibilities, and are not intended to limit the scope of the claims in any way.

Reactive Derivatives and Conjugates of 5 Amino BAPTA

Example 1. Synthesis of 8 BAPTA tetramethyl ester that contains one reactive amine group (Compound I). The synthesis of 5-nitro BAPTA (and 5,5'-dinitro BAPTA) has been reported in a paper by one of the inventors [Cell Calcium 10, 491 (1989)]. However its conversion to 5-amino-BAPTA has not been previously described. 5-Amino-BAPTA tetramethyl ester (Compound I) is synthesized by the following procedure: 1 g of 5-nitro BAPTA tetramethyl ester is dissolved in 10 mL dimethylformamide and this solution is hydrogenated at 40 psi in the presence of 0.1 g 10% palladium on charcoal. The reaction turns colorless and is complete in one hour. TLC in ethyl acetate shows that the 5-nitro BAPTA is completely converted to a low R$_f$, light sensitive product, which reacts with ninhydrin to give a ruddy brown product. The catalyst is filtered through Celite and the filtrate is diluted to 100 mL with ethyl acetate and the solution is washed three times with 200 mL saturated NaCl and once with 200 mL water. The organic phase is dried over Na$_2$SO$_4$ and evaporated. The resulting oil is heated with 50 mL methanol to give a clear brown solution. After cooling on ice overnight, colorless crystals form. These are filtered and dried to give 2.42 g (82% yield) 5-amino BAPTA tetramethyl ester (Compound I). NMR in CDCl$_3$ shows 3.55 ppm 6H, s; 3.60 ppm 6H, s; 4.05 ppm 4H, s; 4.15 ppm 4H, s; 4.3 ppm 4H, m; 6.2 ppm 1 H, d; 6.3 ppm 1H, s; 6.75–6.95 ppm 5H, m.

Example 2. Preparation Of a conjugate of BAPTA linked to a water-soluble polymer by n carboxamide group (Compound II). Compound I is coupled to activated polyacrylic acid through a carboxamide linkage by the following procedure. Polyacrylic acid (1 g of average MW~250,000 from Aldrich Chemical Company, Milwaukee, Wis.)is mixed with 5 mL chloroform. This is cooled in ice and stirred with 50 μL N,N-diisopropyl-N-ethylamine followed by 100 μL isobutyl chloroformate. After 15 minutes 100 mg of Compound 1 is added. The mixture is stirred for 12–15 hours then the chloroform is evaporated. The residue is mixed in water containing 0.1M NaOH to pH 10. The pH is maintained at 10 by addition of 5 M NaOH until no further pH change is observed (~24 hours). The solution is freed from salts by dialysis, first against water, then against 0.1 M $H_3PO_4$. The resulting product is adjusted to pH 7.0 with KOH then lyophilized to Compound II.

Example 3. Synthesis of a BAPTA salt that contains a reactive amine (Compound III). The tetrapotassium salt of 5-amino BAPTA tetramethyl ester (Compound I) is prepared by dissolving 100 mg Compound 1 in a mixture of 1 mL dioxane and 0.5 mL methanol followed by addition of 200 µL of 50% KOH. After hydrolysis at room temperature for ~18 hours, 1 mL deionized water is added. The dioxane and methanol are removed at reduced pressure. Acidification of the solution to ~pH 5 with HCl gives a solid product that is collected by centrifugation. The product is dissolved in water by addition of KOH to pH 8 then lyophilized to an off-white solid (Compound III).

Example 4. Synthesis of a BAPTA salt that contains a reactive isothiocyanate (Compound IV). An aqueous solution of Compound III prepared from 100 mg Compound I according to Example 3 is adjusted to pH 7.0 with dilute HCl. 25 µL of thiophosgene is added. After stirring for 15 minutes the solution is extracted with 3 mL $CHCl_3$ to remove the excess thiophosgene. The aqueous solution of BAPTA isothiocyanate (Compound IV) and salts is lyophilized to a near-colorless solid that is stored desiccated in the freezer. The infrared spectrum in KBr show the presence of a strong isothiocyanate absorption near 2100 $cm^{-1}$. The product can be purified as described in Example 3.

Example 5. Preparation of a conjugate of BAPTA linked to a biopolymer by a thiourea linkage (Compound V). Compound IV is a versatile reactive analog of BAPTA for conjugation of BAPTA to various dyes and polymers. For instance 3.0 mg of Compound IV (used without removal of salts), is conjugated to 10 mg rabbit IgG dissolved in 1 mL sodium bicarbonate buffer pH 9.0. Following reaction for 2 hours, the conjugate is freed from excess reactants and salts by passage through a Sephadex G-25 column eluting with pH 7.5 phosphate buffered saline. Absorbance of the column fractions at 280 nm is used to detect the presence of the labeled IgG. Compound V is isolated as a solid by lyophilization.

BAPTA isothiocyanate can be conjugated to other water soluble polymers such as amino dextrans and amine-derivatized oligonucleotides and nucleic acids by similar chemistry. BAPTA isothiocyanate can be coupled to amine-containing insoluble polymers by a similar reaction in an aqueous or organic solvent followed by washing with an appropriate solvent in which the polymer is insoluble. Alternatively 5-amino BAPTA tetramethyl ester (Compound I) can be converted to the BAPTA tetramethyl ester isothiocyanate by reaction with thiophosgene, this coupled to an amine-containing polymer and the esters removed by hydrolysis in base as described in Example 3. This latter method is not practical with most peptide or protein polymers or other polymers that are particularly sensitive to hydrolysis by base.

Example 6. Synthesis of a BAPTA salt that contains a thiol reactive iodoacetamide (Compound VI). 100 mg of Compound III in 2 mL water is treated by dropwise addition of 100 mg of iodoacetic anhydride dissolved in 1 mL acetonitrile. The crude BAPTA iodoacetamide (Compound VI) is isolated by precipitation with acetone and washed with ether. The product is stored protected from light.

Example 7. Preparation of a conjugate Of BAPTA linked to a liposome by a thioether linkage (Compound VII). Dioleoyl phosphocholine (DOPC) liposomes containing thiolated phosphoethanolamine [derived by reduction of N-((2-pyridyldithio)propionyl)-1,2 -dihexadecanoyl-sn-glycero-3-phosphoethanolamine, triethylammoniumsalt (Molecular Probes, Inc., Eugene, Oreg.) with dithiothreitol according to the method described for this compound by Heath in Methods in Enzymology 149, 111 (1987)] is treated with BAPTA iodoacetamide (Compound 6) at pH 7.6 for 2 hours. The ION—SELECTIVE POLYMERIC liposome (Compound VII) is isolated by purification on a Sephadex G-25 column.

Example 8. Preparation of a conjugate of BAPTA linked to a green fluorescent dye (2',7'-dichlorofluorescein) by a carboxamide linkage (Compound VIII). 5-Carboxy-2',7'-dichlorofluorescein diacetate (Molecular Probes, Inc., Eugene, Oreg.) is dissolved in 20 mL $CH_2Cl_2$ to give a clear solution. The stirred solution is cooled to 0° C. and 0.43 g (4.36 mmoles) triethylamine is added. After five minutes, 0.64 g (4.67 mmoles)isobutyl chloroformate is added and the reaction is stirred at 20° C. for three hours, at which time TLC analysis shows that the starting acid has been completely converted to the mixed anhydride. The solvent is evaporated and redissolved in ethyl acetate. The colorless triethylamine hydrochloride is filtered and the clear filtrate is evaporated at 15° C. to give a colorless oil which dries to a foam under high vacuum. The yield is 2.2 g (3.5 mmoles; 90% yield). NMR in $CDCl_3$ shows 1.55 ppm 6H (s); 2.35 ppm 6H (s); 3.95 ppm 1H (s); 4.4 ppm 2H (q); 6.85 ppm 2H (s); 7.2 ppm 2H (s); 7.85 ppm 1H (s); 8.15 ppm 1H (d); 8.35 ppm (m).

Compound I (1.0 g, 1.82 mmoles) is dissolved in 15 mL $CH_2Cl_2$ to give a clear solution. A solution of the mixed anhydride of 5 carboxy-2',7'-dichlorofluorescein diacetate (1.15 g in 5 mL of $CH_2Cl_2$) is added dropwise to the stirring amine solution over a period of 10 min. The reaction is stirred overnight at room temperature. A TLC the next day (in EtOAc) shows conversion to a new product that on exposure to ammonia vapor yields a colored and fluorescent product ($R_f$=0.25, anhydride $R_f$=0.9). The product is separated on a column packed with 200 mL 35–70µ silica gel packed in and eluted with 1:1:1 $CHCl_3$:hexanes:EtOAc. The pure fractions are evaporated at 30° C. to give 1.35 g (1.27 mmoles; 70.1% yield) of the pure 2',7'-dichlorofluorescein diacetate BAPTA tetramethyl ester. NMR in $CDCl_3$ shows: 2.4 ppm, s 6H; 3.6 ppm, s 12H; 4.15 ppm, s 8H; 4.2–4.35 ppm, d 4H; 6.8 ppm, m 7H; 7.3–7.4 ppm, m 4H; 8.3 ppm, d 1 H; 8.6 ppm, d 2H.

To 1.2 g (1.13 mmoles) of 2',7'-dichlorofluorescein diacetate BAPTA tetramethyl ester in 10 mL dioxane is added 5 mL MeOH followed by 0.6 g (11.3 mmoles) of KOH in 3 mL water is added. The reaction mixture becomes red. The hydrolysis stirs at room temperature overnight. The next day a heavy red precipitate has formed. This is suction filtered then vacuum dried to give a red powder (1.2 g; 1.04 mmoles; 92% of theoretical). The product (Compound VIII) is pure by TLC in 10:10:2:0.2 $CHCl_3$:methanol:water:acetic acid. HPLC shows a purity of 97% (UV detection) and 100% (detected at 490 nm). The extinction coefficient at 505 nm is 105,190 $cm^{-1}M^{-1}$ in methanol.

Example 9. Preparation of a conjugate of BAPTA linked to an orange fluorescent dye (tetramethylrhodamine) by a thiourea linkage (Compound IX). Compound IX is synthesized by either coupling of tetramethylrhodamine isothiocyanate with Compound I (followed by hydrolysis according to Example 3) or by coupling of Compound III with aminotetramethylrhodamine. The final product is purified on Lipophilic Sephadex LH-20.

Example 10. Preparation of a conjugate of BAPTA linked to a red fluorescent polycyclic rhodamine dye (sulforhodamine 101) by a sulfonamide linkage (Compound X). The potassium salt (Compound X) is prepared by reaction of Compound II with the sulfonyl chloride of sulforhodamine 101 followed by hydrolysis of the methyl esters according to Example 3.

Example 11. Preparation of a conjugate of BAPTA linked to a blue fluorescent coumarin dye (7-diethylaminocoumarin-3-carboxylic acid) by a carboxamide linkage (Compound XI). 100 mg 7-diethylaminocoumarin-3-carboxylic acid (Molecular Probes, Inc.; Eugene, Oreg.) is dissolved in 2.0 mL oxalyl chloride and warmed to 40° C. for 20 minutes. The oxalyl chloride is evaporated and the resulting yellow acid chloride is dissolved in 1 mL dimethylformamide and added dropwise to a solution of 95 mg Compound 1 in I mL of cold dimethylformamide. The amine on the BAPTA reacts with the acid chloride to give a blue fluorescent product with a high $R_f$. The coumarin BAPTA tetramethyl ester is purified on 150 mL silica gel eluted with 1:1:1 ethyl acetate:$CHCl_3$: hexanes. The pure fractions are combined and evaporated to 120 mg of a yellow semi-solid. This is resuspended in 1 mL dioxane and I mL methanol. 0.06 g KOH in 0.3 mL water is added and the hydrolysis is stirred 16 hours at room temperature. The solvents are evaporated and the semi-solid is dissolved in 2 mL deionized water and purified on 75 g Sephadex LH-20. The fluorescent band is isolated and lyophilized to 75 mg of a light yellow powder (Compound XI).

Example 12. Synthesis of a BAPTA tetraacetoxymethyl ester that contains a reactive amine (Compound XIII). 5—Nitro BAPTA tetramethyl ester (2.0 g, 3.46 mmoles) [Cell Calcium 10, 491 (1989)] is dissolved in 10 mL dioxane to give a clear yellow solution. Methanol (10 mL) is added, followed by 22.5 g (34.6 mmoles) 40% aqueous tetrabutylammonium hydroxide. The hydrolysis reaction is stirred 14 hours at room temperature and is then evaporated to give a yellow oil. This is dried under high vacuum for 2 hours. The oil is redissolved in 25 mL $CH_2Cl_2$ and 5.3 g (34.6 mmoles) bromomethyl acetate is added followed by 0.9 g (6.9 mmoles) N,N-diisopropyl—N-ethylamine. The reaction is stirred for ~12 hours at room temperature. A TLC in ethyl acetate:hexanes 1:1 shows that the salt is converted to a yellow product with an $R_f$ of ~0.6. The yellow solution is loaded directly onto a silica gel column packed and eluted in ethyl acetate/$CHCl_3$/hexanes 1:1:1. The pure product-containing fractions from the column are combined and evaporated to a clear yellow oil. The oil is crystallized from 20 mL methanol to give 2.03 g (72.4% of theoretical) of 5-nitro BAPTA tetraacetoxymethyl ester (Compound XII) as a light yellow powder. NMR in $CDCl_3$ shows 12 H at 2.1 ppm (s); 4.2 ppm (s) 4 H; 4.3 ppm (s) 4H; 4.35 to 4.45 ppm 4H (d); 5.1 ppm 4H (s); 5.2 ppm 4H (s); 6.2 ppm 1H (d); 6.8 to 7.0 ppm 4H (m); 7.65 ppm 1H (s); 7.85 ppm 1H (d).

Hydrogenation of 1.1 g (1.36 mmoles) of 5-nitro BAPTA tetraacetoxymethyl ester dissolved in 25 mL dimethylformamide over 0.3 g 10% palladium on charcoal for 3 hours at 35 psi yields a colorless solution. TLC of the reaction in $CHCl_3$:methanol 9:1 shows that all the starting material is converted to a lower $R_f$ light-sensitive product that reacts with ninhydrin to give a red-brown product. The reaction is filtered through diatomaceous earth. The colorless filtrate is diluted with 120 mL ethyl acetate, washed three times with 200 mL saturated NaCl and one time with 200 mL water. The organic layer is dried over $Na_2SO_4$ and evaporated to a thick tan oil of 5-amino BAPTA tetraacetoxymethyl ester (Compound XIII) (1.07 g; 99% yield). TLC purity ~95%. NMR in $CDCl_3$ shows 2.1 ppm 12H (s); 4.1 ppm 4H (s); 4.2 ppm 4H (s); 4.35 ppm 4H m); 5.15 ppm 4H (s); 5.2 ppm 4H (s); 6.2 ppm 1H (d); 6.35 ppm 1H (s); 6.8 to 7.0 ppm (m) 5H (m).

Example 13. Preparation of a conjugate of BAPTA tetraacetoxymethyl ester linked to an orange fluorescent dye (tetramethylrhodamine) by a thiourea linkage (Compound XIV). Tetramethylrhodamine-5-isothiocyanate (0.25 g) (Molecular Probes, Inc., Eugene, Oreg.) is dissolved in 5 mL dimethylformamide to give a red solution. This is combined with 120 mg 5-amino BAPTA tetraacetoxymethyl ester (Compound XIII) dissolved in 1 mL dimethylformamide. The reaction is stirred at room temperature for 2 hours, at which point a TLC in 10% methanol: 1% acetic acid:89% $CHCl_3$ shows a new, orange fluorescent product. After stirring overnight at room temperature the reaction is diluted with 100 mL ethyl acetate. The resulting solid is filtered to give 225 mg of crude product. This solid is purified on 150 mL 35 to 70μ silica gel using 10% methanol: 1% acetic acid:89% $CHCl_3$ to elute 107 mg of a red solid (Compound XIV). This is pure to TLC and ~100% pure by HPLC measured at both 254 and 540 nm. The extinction coefficient in methanol at 540 nm is 78,200 $cm^{-1}M^{-1}$. NMR in $CDCl_3$ shows 2.1 ppm 12H (s); 3.05 ppm 12H (s); 4.2 ppm 12H (m); 5.6 ppm 4H (s); 5.7 ppm 4H (s); 6.5 ppm 2H (s); 6.6–6.7 ppm 3H (2d); 6.8 ppm 5H (m); 7.2 ppm 2H (m); 8.1 ppm 1H (s).

Example 14. Preparation of a conjugate of BAPTA tetraacetoxymethyl ester linked to a red fluorescent polycyclic rhodamine dye (sulforhodamine 101) by a sulfonamide linkage (Compound XV). The sulfonyl chloride of sulforhodamine 101 (Texas Red® sulfonyl chloride, Molecular Probes, Inc.; Eugene, Oreg.) (0.90 g, 1.44 mmoles) is added as a powder over about 3 minutes to a solution of 0.71 g (0.91 mmoles) Compound XIII in 3 mL dimethylformamide with vigorous stirring. The purple solution is stirred at room temperature for ~13 hours. TLC in $CHCl_3$: methanol 4:1 shows a new purple product. The reaction is poured into 300 mL water and stirred for ½ hour. The resulting precipitate is filtered and dried to give 0.7 g of a purple powder. This solid is dissolved in 10 mL CHCl3 and is loaded onto a column of 120 mL 35 to 70μ silica gel. The red product is eluted with 10% methanol: 1% acetic acid:89% $CHCl_3$. The product-containing fractions are combined and washed with saturated sodium bicarbonate and water. The organic layer is dried over sodium sulfate and evaporated to give 70 mg of a metallic purple solid. The solid is further purified on 100 mL 35 to 70μ silica gel eluted with 8% methanol: 0.5% acetic acid: 91.5% $CHCl_3$ and the pure fractions are evaporated to give 105 mg (7.6% yield) of pure product (Compound XV). The HPLC purity is 94% measured at 580 nm the extinction coefficient measured at 583 nm in methanol is about 90,000 $cm^{-1}M^{-1}$.

Reactive Derivatives and Conjugates of 5,5'-diamino BAPTA

Example 15. Synthesis of a BAPTA tetramethyl ester that contains two reactive amine groups (Compound XVI).

11.0 g (17.7 mmoles) of 5,5'-dinitro BAPTA tetramethyl ester [Cell Calcium 10, 491 (1989)] is dissolved in 200 mL dimethylformamide and the solution is hydrogenated at 40 psi for three hours in the presence of 0.8 g 10% palladium on charcoal. When complete, the reaction is filtered through diatomaceous earth. The clear filtrate is diluted to 500 mL with ethyl acetate and the solution is washed three times with saturated NaCl and once with water. The organic layer is dried over $Na_2SO_4$ and evaporated under reduced pressure to a grey oil. Trituration with methanol yields 7.0 g (12.4 mmoles; 70.3% yield) of 5,5'-diamino BAPTA, tetramethyl ester (Compound XVI), ~95% pure by TLC in 5% methanol:$CHCl_3$.

Example 16. Preparation of a conjugate of BAPTA linked to two identical green fluorescent dyes (2',7'-dichlorofluorescein) by carboxamide linkages (Compound XVII). To a solution of 0.26 g (0.47 mmoles) Compound XVI in 10 mL dichloromethane is added 0.83 g (1.25 mmoles) of the mixed anhydride of 5-carboxy-2',7'-dichlorofluorescein diacetate (Example 13) followed by 200 μL of triethylamine. After 3 hours at room temperature the TLC in 5% MeOH/$CHCl_3$ after exposure to ammonia vapors shows predominantly a single orange product. The organic layer is washed with dilute sodium bicarbonate followed by water. The solution is dried over sodium sulfate then evaporated. The residue is chromatographed on 125 mL of silica gel prepared in and eluted with 1% methanol in chloroform. The product-containing fractions are evaporated to ~750 mg of an orange powder that is >90% pure by HPLC. Rechromatography yields a product that is >98% pure by HPLC. Hydrolysis with KOH in aqueous methanol containing ~10% dioxane by the method described in Example 3 yields the octapotassium salt (Compound XVII).

Example 17. Synthesis of a BAPTA tetraacetoxymethyl ester that contains two reactive amine groups (Compound XVIII). Hydrogenation of 5,5'-dinitro BAPTA tetraacetoxymethyl ester (Molecular Probes, Inc.; Eugene, Oreg.) and workup as described in Example 1 yields >80% Compound XVIII.

Example 18. Synthesis of a conjugate of BAPTA tetramethyl ester that contains one green fluorescent (2',7'-dichlorofluorescein) dye linked by a carboxamide linkage and one reactive amine group (Compound (XIX). 5,5'-Diamino BAPTA tetramethyl ester (Compound XVIII) (0.35 g, 0.64 mmoles) is dissolved in 5 mL dichloromethane. One equivalent of the mixed anhydride of 5-carboxy-2',7'-dichlorofluorescein diacetate (0.43 g, 0.64 mmoles) (Example 13) is added as a solid in three portions over ~10 min. The reaction is stirred at room temperature for three hours, then is stored in an ice bath overnight. TLC using 5% MeOH/$CHCl_3$ shows a new, ninhydrin positive quenching product formed with an $R_f$ of ~0.3, which becomes orange and weakly fluorescent on exposure to ammonia vapors. The mixed anhydride has an $R_f$ of about 0.8 in this solvent and the diamine stays near the origin. Some of each of the starting materials remain. The reaction is loaded directly onto a column packed with 150 mL silica (40–70μ) and eluted with 3% MeOH/$CHCl_3$. The purest fractions are combined and evaporated. The acetate esters are hydrolyzed by stirring overnight with 5% ammonium hydroxide in 3:1 dioxane:methanol. The precipitate that forms is filtered. Analysis by TLC shows it to contain ~85% of the desired product and about ~15%) product containing two dyes. The solid is dissolved in $CHCl_3$ containing ~15% MeOH and purified on 100 mL silica (40–70μ) packed and eluted in 1% AcOH:10% MeOH:$CHCl_3$. The product is eluted with 1% AcOH to give 285 mg (43% yield) the tetramethyl ester of amino BAPTA containing a single 2',7'-dichlorofluorescein dye (Compound XIX).

Example 19. Synthesis of a conjugate of BAPTA that contains one green fluorescent (2',7'-dichlorofluorescein) dye linked by a carboxamide linkage and one reactive amine group (Compound XX). Hydrolysis of Compound XIX according to Example 3 yields the fluorescent hexapotassium salt of a green fluorescent amino BAPTA (Compound XX).

Example 20. Synthesis of a conjugate of BAPTA that contains one green fluorescent (2',7'-dichlorofluorescein) dye linked by a carboxamide linkage and one reactive isothiocyanate group (Compound XXI). The green fluorescent BAPTA isothiocyanate potassium salt is synthesized starting with Compound XX by the method described in Example 4.

Example 21. Synthesis of a conjugate of BAPTA tetramethyl ester that contains one green fluorescent (2',7'-dichlorofluorescein) dye linked by a carboxamide linkage and one reactive isothiocyanate group (Compound XXII). The tetramethyl ester of BAPTA isothiocyanate containing a 2',7'-dichlorofluorescein dye (Compound XXII) is synthesized by treating a suspension of 0.13 g (0.13 mmoles) of Compound XX in 10 mL acetone with 10 μL (0.14 mmoles) thiophosgene for 30 minutes at 30° C. The light yellow solution gives two products $R_f$~0.9 and $R_f$~0.5 in 1% AcOH:9% MeOH:$CHCl_3$. Both products are nearly colorless. The solution is evaporated to a light oil. This is washed with 10 mL methanol. The insoluble solid is centrifuged to give a tan solid. The solid is redissolved in $CHCl_3$ and evaporated to 125 mg (88% yield) of the lower $R_f$ product (Compound XXII), which reacts with n-butyl amine to give a new product on TLC.

Example 22. Preparation of a conjugate of BAPTA with one green fluorescent (2',7'-dichlorofluorescein) dye linked by a carboxamide linkage and a water-soluble polymer linked by a carboxamide linkage (Compound XXIII). The fluorescent BAPTA isothiocyanate tetramethyl ester, XXII (30 mg, 0.028 mmoles) is dissolved in 1 mL dimethylformamide. This solution is added in one portion to a stirring solution of 0.18 g (2.6 μmoles) 70,000 MW amino dextran (approximately 30 moles of amines/70,000 g of dextran, Molecular Probes, Inc.; Eugene, Oreg.) in 2 mL DMSO. The dextran is warmed slightly to give a clear solution. The isothiocyanate is light yellow until it reacts with the dextran, when it becomes very red and fluorescent. The reaction is stirred overnight at room temperature. The crude conjugate is added to 100 mL vigorously stirring acetone. The solid is filtered through a fritted glass funnel and the red solid is redissolved in 10 mL deionized water.

The methyl esters are hydrolyzed as described in Example 3. Once the pH has stopped dropping the solution is dialyzed against deionized water for three days using a 12–14,000 MW cutoff dialysis membrane. The solution is lyophilized to give 0.16 g (2.3 μmoles, 89% yield) of an orange solid (Compound XXIII).

Example 23. Preparation of a conjugate of BAPTA with one green fluorescent (2',7'-dichlorofluorescein) dye linked by a carboxamide linkage and one orange fluorescent dye (tetramethylrhodamine) linked by a thiourea and a carboxamide linkage (Compound XXIV). Isothiocyanate (Compound XXII) is reacted with 5-(and-6)-((N-(5-aminopentyl)amino)carbonyl)tetramethylrhodamine (tetramethylrhodamine cadaverine)(Molecular Probes, Inc;

Eugene, Oreg.). The thiourea product is purified by preparative TLC using CHCl$_3$: MeOH:AcOH:H$_2$O 75:20:4:1. The product band is scraped from the sheets, dissolved in dioxane:MeOH 1:1 and treated with 1/10 volume of 20% KOH in water. After ~12 hours at room temperature the solution is evaporated, the solid is dissolved in a small volume of water and this is purified on a column of Sephadex LH-20. The product containing fractions are analyzed spectroscopically, the appropriate fractions are combined and lyophilized to a red solid.

Reactive Derivatives and Conjugates of 4-hydroxy BAPTA

Example 24. Synthesis of a BAPTA tetramethyl ester that contains a phenolic reactive group (Compound XXV). A hydroxy derivative of BAPTA (4-hydroxy-BAPTA) is synthesized by hydrogenation of one of the key intermediate in the synthesis of the Ca$^{2+}$ indicator fura-2 [U.S. Pat. No. 4,603,209]. For instance 9.8 g of 4-benzyloxy-5'-methyl BAPTA tetramethyl ester is hydrogenated in 50 mL glacial acetic acid in the presence of 0.3 g 10% palladium on charcoal at 40 psi hydrogen pressure for four hours. The reaction is filtered through a pad of Celite to remove the catalyst and the yellow filtrate is evaporated under reduced pressure to give a light brown oil. This is triturated with 50 mL methanol to yield 7.2 g of 4-hydroxy BAPTA tetramethyl ester as a colorless solid (Compound XXV).

Example 25. Synthesis of a BAPTA tetramethyl ester that contains an amine-reactive carboxylic acid (Compound XXVII) and its succinimidyl ester (Compound XXVIII). Compound XXV is reacted at room temperature for ~18 hours with 0.39 g t-butyl bromoacetate in 5 mL dimethylformamide in the presence of 0.75 g potassium carbonate. The crude product is precipitated with water and recrystallized from methanol yielding 1.4 g 4 -(t-butoxycarbonylmethoxy)-BAPTA tetramethyl ester (Compound XXVI). The t-butyl ester is selectively removed by treating 0.5 g 4-(t-butoxycarbonylmethoxy)-BAPTA with 0.4 mL trifluoroacetic acid in 3 mL methylene chloride. The reaction is stirred for ~18 hours at room temperature until thin layer chromatography (TLC) using 5% methanol in CHCl$_3$ shows it to be complete. The solvent is evaporated to a clear oil of 4-(carboxymethoxy)-BAPTA tetramethyl ester (Compound XXVII). This product is dried completely and used without further purification.

The carboxylic acid of Compound XXVII can be activated for coupling to nucleophilic groups by several methods. For instance the amine reactive BAPTA succinimidyl ester (Compound XXVIII) is prepared by dissolving 0.9 g of Compound III in 3 mL dimethylformamide containing 0.17 g N-hydroxysuccinimide. A solution of 0.34 g dicyclohexylcarbodiimide (DCC) in 0.8 mL dimethylformamide is added and the reaction is stirred for ~12 hours until the TLC in ethyl acetate:CHCl$_3$ 1:1 shows it to be complete. The reaction is cooled to 4° C. and the resulting dicyclohexyl urea precipitate is filtered. Compound XXVIII is precipitated with ether, washed with ether and vacuum dried.

Example 26. Preparation of a conjugate of BAPTA linked to a water-soluble polymer by an ether and a carboxamide group (Compound XXIX). Succinimidyl esters are useful derivatives for forming amides by reaction with aliphatic amines. For instance, 0.1 g of Compound XXV is mixed with 0.50 g of ~10,000 MW amino dextran (Molecular Probes, Inc., Eugene, Oreg.) that contains an average of 3 moles of primary aliphatic amines/10,000 g of dextran in DMSO. After 14 hours at room temperature, the conjugation reaction is poured into 50 mL stirring acetone. The suspension is centrifuged and the resulting colorless gel dissolved in 10 mL deionized water. To hydrolyze the methyl esters on the BAPTA chelator the pH is continuously maintained at 11.0 by addition of 40% KOH solution until the pH remains stable (~18 hours). The pH is adjusted with HCl to 8.0 and the solution is transferred to a dialysis membrane tubing with a 3,500 MW cutoff. The solution is dialyzed for two days versus deionized water to remove the excess salts and a final dialysis with pH 7.5 KOH in deionized water to ensure that the counterion is uniformly potassium. The clear solution is lyophilized to give 0.5 g colorless BAPTA-dextran (Compound XXIX).

Example 27. Preparation of a conjugate of BAPTA linked to a water-insoluble polymer linked by an ether group (Compound XXX). The reactive phenolic BAPTA derivative (Compound XXV) is a versatile intermediate for forming COVALENT LINKERS. For instance heating 0.5 g Compound XXV with 1 g of the insoluble chloromethyl polystyrene-2% divinylbenzene polymer ("Merrifield's Resin;" Sigma Chemical Co.) for 10–15 hours in 10 mL dimethylformamide in the presence of 0.5 g potassium carbonate results in formation of a stable ether linkage between the BAPTA tetra ester and the polymer. The resin is filtered and washed with ethyl acetate and acetone. Following air drying it is stirred at room temperature with 10% methanolic KOH for ~48 hours resulting in an insoluble ION—SELECTIVE POLYMER where the COVALENT LINKER is a hydrolytically stable ether. Methyl esters are preferred as temporary protecting groups on the tetracarboxylate portion of the BAPTA chelator because of their ease of hydrolysis by base.

Example 28. Preparation of a conjugate of BAPTA linked to a water-insoluble polymer by an ether and a carboxamide group (Compound XXXI). Compound XXVIII is coupled to aminoethyl polyacrylamide (Biogel P-2, Bio-Rad Corp.; Dublin, Calif.) by a reaction analogous to that described in Example 26. In this case it is only necessary (after labeling and hydrolysis) to wash the ION—SELECTIVE POLYMER linked by an ether-carboxamide COVALENT LINKER with water to isolate Compound XXXI.

Figure 6:
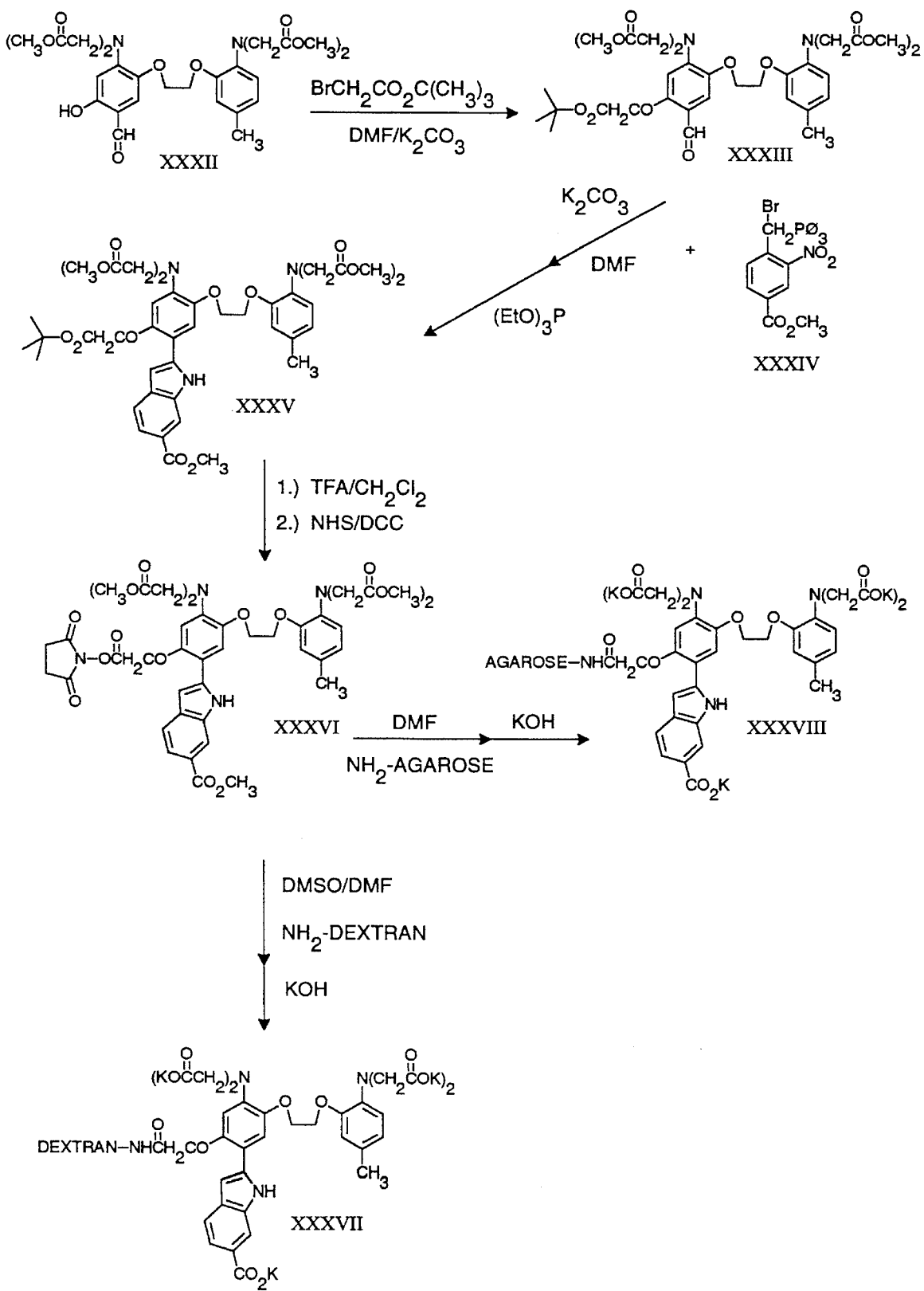
FIG. 6: Synthetic route to reactive derivatives and conjugates of 5-indolyl BAPTA

FIG. 6—Reactive derivatives and conjugates of 5-indolyl BAPTA

Example 29. Synthesis of a conjugate of BAPTA tetramethyl ester with one blue fluorescent (indolyl) dye and a carboxylic acid and its succinimidyl ester (Compound XXXVI). An intermediate from the synthesis of the Ca$^{2+}$ indicator commonly known as "fura-2" [U.S. Pat. No. 4,603,209] is used as the starting material for preparation of an appropriately protected reactive form of a second Ca$^{2+}$ indicators commonly known as "indo-1" [U.S. Pat. No. 4,603,209]. 4-Hydroxy-5-formyl-5'-methyl BAPTA tetramethyl ester (XXVI in U.S. Pat. No. 4,603,209 or XXXII in FIG. 6] (25 g, 42 mmoles) is dissolved in 50 mL dimethylformamide containing 11.6 g (84 mmoles) potassium carbonate and 16.5 g (85 mmoles) tert-butyl bromoacetate. The stirred mixture is heated at 70° C. for two hours. The reaction is cooled to room temperature and diluted with 250 mL ethyl acetate. The solution is washed three times with brine and once with water. The organic layer is dried over sodium sulfate and evaporated at reduced pressure to a grey oil. Crystallization from methanol gives 25 g (85% yield) of colorless crystals of 4-(t-butoxycarbonylmethoxy)-5-formyl-5'-methyl BAPTA tetramethyl ester that is pure by TLC (ethyl acetate:hexanes 1:1).

4-(t-Butoxycarbonylmethoxy)-5-formyl-5'-methyl BAPTA tetramethylester, Compound XXXIII (25 g, 35.5 mmoles) is reacted with 29 g (53.3 mmoles) 4-methoxycarbonyl benzyltriphenylphosphonium bromide [XIV in U.S. Pat. No. 4,603,209 or XXXIV in FIG. 6] by dissolving both in 70 mL dimethylformamide in the presence of 15 g (0.106 mmoles) potassium carbonate and heating to 90° C. for two hours. TLC (ethyl acetate:hexanes 1:1) shows complete conversion of the product to the corresponding colored vinyl derivative. The reaction is cooled, diluted to 300 mL with ethyl acetate, washed three times with brine and once with water. The organic layer is evaporated at reduced pressure to a red oil. This is purified on 350 mL silica gel (40–70μ) prepared in and eluted with ethyl acetate:hexanes:CHCl$_3$ 1:1:1. The pure column fractions are evaporated to a red oil (18.2 g). This oil is dissolved in 50 mL redistilled triethyl phosphite and refluxed for three hours until the solution is nearly colorless. TLC showed complete conversion of the yellow starting product to the colorless, blue fluorescent derivative. The triethyl phosphite is removed under vacuum while the reaction is still near 80° C. The resulting grey oil is recrystallized from boiling methanol and filtered after cooling to 15 g of crude product. This is further purified by column chromatography eluting in 1:1:1 ethyl acetate:hexanes CHCl$_3$. Pure fractions are combined, evaporated and triturated with methanol to obtain 4-(t-butoxycarbonylmethoxy)-5-( 6-carbomethoxy-2-indolyl)-5'-methyl BAPTA tetramethyl ester (XXXV in FIG. 6) as a colorless solid, pure to TLC.

The tert-butyl protecting group of 4-(t-butoxycarbonylmethoxy)-5-(6-carbomethoxy-2-indolyl)-5'-methyl BAPTA tetramethyl ester (XXXV in FIG. 6) is removed by dissolving 2.0 g of the t-butyl ester in 20 mL methylene chloride and adding 6 mL trifluoroacetic acid. After stirring the solution at room temperature overnight the TLC shows complete hydrolysis of the t-butyl ester. The reaction is evaporated to a brown oil. This is triturated with 100 mL methanol to give 2.2 g of a moist yellow solid. This is immediately dissolved in 10 mL chloroform and purified on 150 mL silica gel eluted with 10% methanol, 1% acetic acid in chloroform. The pure fractions of 4-(carboxymethoxy)-5-(6-carbomethoxy-2-indolyl)-5'-methyl BAPTA tetramethyl ester are combined and evaporated to a clear oil.

The amine reactive succinimidyl ester of 4-(carboxymethoxy)-5-(6-carbomethoxy-2 -indolyl)-5'-methyl BAPTA tetramethyl ester is synthesized from 0.45 g (0.567 mmoles) of the carboxylic acid dissolved in 3.5 mL CH$_2$Cl$_2$ and 0.13 g (1.13 mmoles) N-hydroxy succinimide. The reaction is stirred for 30 minutes then 0.23 g dicyclohexyl carbodiimide dissolved in 0.8 mL CH$_2$Cl$_2$ is added in one portion to the stirring solution. After stirring for 16 hours at room temperature 0.14 g colorless precipitate of dicyclohexyl urea is filtered. The filtrate is evaporated to a colorless semi-solid of 4-(carboxymethoxy)-5-(6-carbomethoxy-2-indolyl)-5'-methyl BAPTA tetramethyl ester, succinimidyl ester ("protected indo 1 succinimidyl ester;" Compound XXXVI) that is about 80% pure by TLC.

Example 30. Preparation of a reactive BAPTA with one blue fluorescent (indolyl) dye and a water-soluble polymer linked by an ether and a carboxamide group (Compound XXXVII). A solution of 0.14 g (0.16 mmoles) of the protected indo 1 succinimidyl ester (Example 29) in 4 mL dimethylformamide is added to a solution of 1 g (14.3 μmoles) 70,000 MW amino dextran substituted by ~30 amines/dextran (Molecular Probes, Inc.; Eugene, Oreg.) that is dissolved in 10 mL anhydrous DMSO. After stirring for ~24 hours at room temperature the reaction mixture is added to 250 mL rapidly stirring acetone to precipitate the dextran. The cream-colored gel is filtered and redissolved in 40 mL deionized water. The solution is hydrolysed and Compound XXXVII is isolated as described in Example 22.

Example 31. Preparation of a reactive BAPTA with one blue fluorescent (indolyl) dye and a water-insoluble polymer linked by an ether and a carboxamide group (Compound XXXVIII). Compound XXXVI (25 mg) is dissolved in 1.0 mL dimethylformamide and this solution is added dropwise over three minutes to a stirred suspension of 10 mL amino agarose that contains ~7 μM amines/mL of wet gel (Sigma Chemical; Company, St. Louis, Mo.) in 25 mL dimethyl formamide. After stirring the suspension at room temperature for ~16 hours the solid is centrifuged to a cream-colored gel. This is washed 3×25 mL acetone to remove any unreacted dye then resuspended in 30 mL deionized water. The pH is brought to 12.0 with small additions of 40% potassium hydroxide solution and the suspension is stirred ~14 hours at room temperature. The suspension is washed four times with pH 9 KOH and stored as a suspension in 25 mL deionized water at pH 7.5.

Reactive Derivatives and Conjugates of Oxazolyl-furan BAPTA and Conjugates

Figure 7:
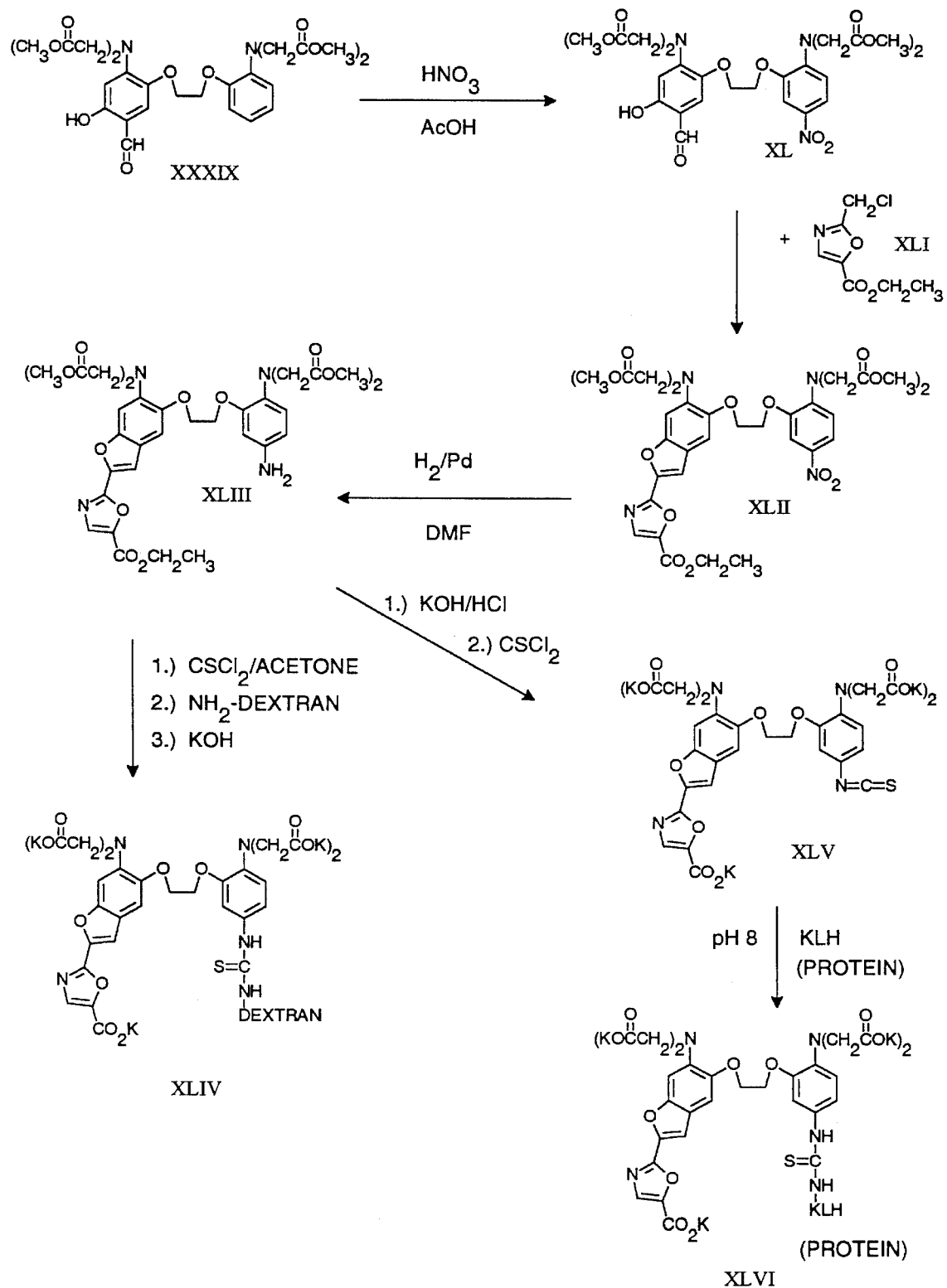
FIG. 7: Synthetic route to reactive derivatives and conjugates of oxazolyl-furan BAPTA

Example 32. Synthesis of a reactive BAPTA tetramethyl ester with one green fluorescent (oxaxolyl-furan) dye and a reactive amine group (Compound XLIII). The precursor to an appropriately-protected reactive amine analog of the common Ca$^{2+}$ indicator fura-2 is synthesized by a route analogous to that used to prepare fura-2 in U.S. Pat. No. 4,603,209 except that the 5'-methyl group in fura-2 is replaced by the reactive amino group as follows. 2.0 g (3.47 mmoles) of 4-hydroxy-5-formyl BAPTA tetramethyl ester (XXXIX in FIG. 7) is dissolved in 30 mL warm AcOH. This product is nitrated by reaction with 0.27 g (4.17 mmoles) 70% nitric acid that is added dropwise over ~5 min. TLC in 1:1 ethyl acetate:hexanes shows that all the starting BAPTA has been converted to a lower R$_f$, yellow-colored product. The reaction is poured into 150 mL of cold water, stirred for 1 hour and filtered to give 1.7 g of a brown solid (79% crude yield) after drying overnight under vacuum. This material is purified on 150 mL of 45–90μ silica gel packed in and eluted with 1:1:1 EtOAc:CHCl$_3$: hexanes. Pure factions are combined and evaporated to a light yellow oil. This crystallizes on washing with methanol to give 0.89 g (41% yield) of pale yellow crystals of 4-hydroxy-5-formyl-5'-nitro BAPTA tetramethyl ester (XL in FIG. 7).

4-Hydroxy-5-formyl-5'-nitro BAPTA tetramethyl ester (XL in FIG. 7) (0.5 g, 0.8 mmoles) is dissolved in 2 mL dry dimethylformamide and warmed to dissolution. Potassium carbonate is added followed by 0.18 g (0.88 mmoles) 3-methyl-2-chloromethyl oxazole-5-carboxylate, ethyl ester (XLI). The reaction is heated to 106° C. for 1.5 hours at which point TLC analysis (1:1 ethyl acetate:hexanes) shows good conversion to the slightly blue fluorescent, yellow-colored product. The solution is diluted with 100 mL EtOAc and washed three times with 100 mL brine and once with 100 mL water. The organic layer is evaporated under reduced pressure to a yellow-brown oil. This is heated to boiling with 30 mL methanol for two minutes. Yellow crystals (370 mg; 60% yield) of "5'-nitro-fura" ethyl ester tetramethyl ester (XLII in FIG. 7) form after cooling overnight.

Hydrogenation of 175 mg (0.45 mmoles) Compound XLII in 5 mL dimethylformamide over 0.05 g 10% palladium on charcoal for two hours gives a clear solution with blue fluorescence. TLC (10% methanol:90% $CHCl_3$) shows complete conversion of the nitro compound to a lower $R_f$, fluorescent product that reacts on heating with ninhydrin. The reaction is filtered through diatomaceous earth to remove the catalyst, the solution is evaporated and the product is crystallized from 7 mL methanol to give 120 mg of tan-grey crystals of "5'-amino fura" ethyl ester tetramethyl ester (73% yield). The product (Compound XLIII) is pure on TLC (10% methanol/$CHCl_3$).

Example 33. Synthesis of a reactive BAPTA tetramethyl ester with one green fluorescent (oxazolyl-furan) dye and a reactive isothiocyanate group Compound XLIII (100 mg, 0.138 mmoles) is dissolved in 3.5 mL acetone with slight heating to give a dark grey solution. Thiophosgene (13 μL, 0.16 mmoles) is added to give a grey-green solution. TLC (1:1 EtOAc:hexanes) after stirring for 1.5 hours shows that no amine remains. The product is precipitated with hexanes at 0° C. Fura ethyl ester tetramethyl ester isothiocyanate (XLII in FIG. 7) is filtered the next day to give 83 mg (79% yield) grey crystalline solid, pure by TLC. The isothiocyanate is much more fluorescent that the amine and moves with a higher $R_f$ on TLC.

Example 34. Preparation of a conjugate of BAPTA linked to one green fluorescent (oxaxolyl-furan) dye and a water-soluble polymer by a thiourea linkage (Compound XLIV). 80 mg (0.104 mmoles) of the amine reactive isothiocyanate from Example 33 is dissolved in 1 mL dimethylformamide to give a yellow solution which is added dropwise over ~1 minute to a solution of 650 mg (9.2 μmoles) ~70,000 MW amino dextran containing ~30 amines/mole dextran dissolved in 3 mL DMSO. After stirring the reaction overnight at room temperature the TLC in 10:10:2:0.2 $CHCl_3$:methanol:water:acetic acid shows all fluorescence remains at the origin. The product is precipitated by addition to 100 mL of acetone with stirring. The yellowish precipitate is filtered then redissolved in a minimum volume of deionized water (~15 mL). The esters are hydrolyzed and the product is isolated as described in Example 9. The final dialysis is against pH 7.5 KOH in deionized water to ensure that the counterion is uniformly potassium. The dialysis solution is then lyophilized to give 1.16 g of Compound XLIV as a yellowish solid.

Example 35. Synthesis of a reactive BAPTA ester with one green fluorescent (oxaxolyl-furan) dye and a reactive amine group Hydrolysis of Compound XLIII according to Example 3 produces 5'-amino fura pentapotassium salt.

Example 36. Synthesis of a reactive BAPTA ester with One green fluorescent (oxaxolyl-furan) dye and a reactive isothiocyanate group (Compound XLV). Conversion of Compound XLIII to the reactive fura isothiocyanate, pentapotassium salt proceeds as described in Example 4.

Example 37. Preparation of a conjugate of BAPTA with one green fluorescent (oxaxolyl-furan) dye and a biopolymer linked by a thiourea linkage (Compound XLVI). Compound XLV ( 10 mg) is added to a solution of 25 mg keyhole limpet hemocyanin (KLH, Calbiochem, La Jolla, Calif.) in 1.5 mL sodium bicarbonate buffer, pH 9. The reaction is stirred at room temperature for ~14 hours. It is then diluted with 2.0 mL deionized water and applied to a Sephadex G-25 gel filtration column eluted with pH 7.5 phosphate buffered saline to remove any unreacted dye. The fluorescent KLH band is collected and lyophilized to give a nearly colorless powder (Compound XLVI).

Ion Binding Properties of BAPTA Conjugates

Figure 8:
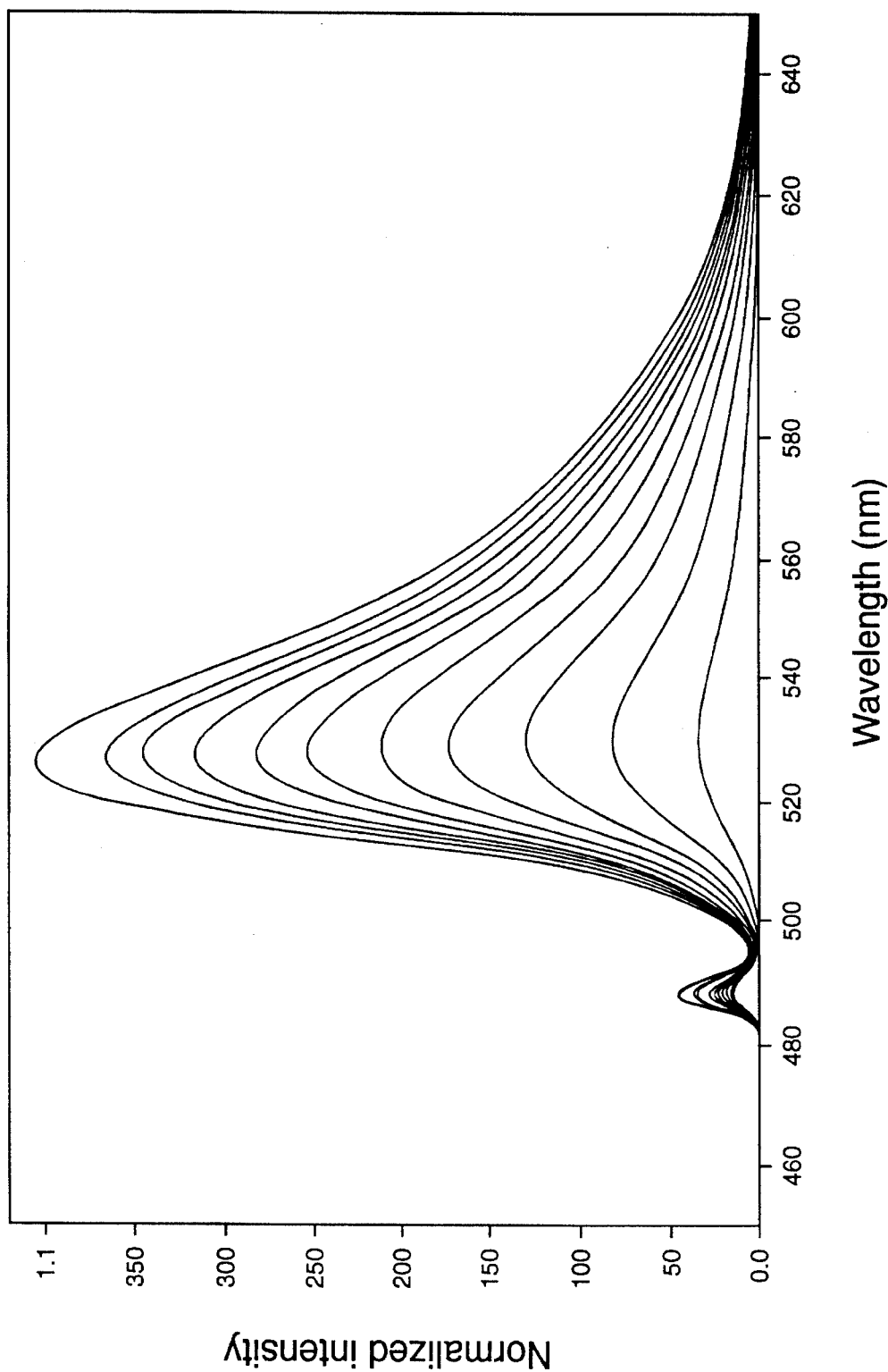
FIG. 8: Calcium Response of Compound VIII: The emission spectra of this indicator is described in Example 38

Example 38. $Ca^{2+}$ binding affinity of a conjugate of BAPTA linked to a green fluorescent dye (2',7'-dichlorofluorescein) by a carboxamide linkage (Compound VIII). The fluorescence response and dissociation constant of the fluorescent BAPTA conjugates as described in Examples 8,9,10 and 11 are determined using the Calcium Calibration Buffer Kit II (Molecular Probes, Inc.; Eugene, Oreg.) which is based on a method described in Methods in Enzymology 172, 230 (1989). For example, 1 mg compound VIII is dissolved in deionized water and 5 μL diluted into three milliliters of each of two buffers which are cross diluted to arrive at a series of $Ca^{2+}$ concentrations between zero and 35 μM. Emission spectra of the dye solutions are scanned between dilutions to generate a family of curves. Each of these curves has a fluorescence emission at approximately 530 nm with an increase in fluorescence emission intensity with increasing $Ca^{2+}$ concentration (see FIG. 8). This intensity change is plotted against the concentration of free $Ca^{2+}$ to give a value for the dissociation constant of the indicator. For Compound VIII, the intensity increase is approximately 12-fold as $Ca^{2+}$ levels increase from zero to 35 μM. The calculated dissociation constant at 20° C. is 189 nM. Similar fluorescence measurements are used to produce the data for Compounds IX, X, and XVII listed in Table 3.

Example 39. Determining the ion selectivity and affinity of water-soluble ion selective polymers. The affinity of conjugates of BAPTA with water-soluble polymers such as that described in Example 12 is measured using the Calcium Calibration Buffer Kit II (Molecular Probes, Inc.; Eugene, Oreg.) which is based on a method described in Methods in Enzymology 172, 230 (1989). The absorption spectra of the solutions of the conjugate of BAPTA with a water-soluble dextran (Example 28) are scanned form 200 to 400 nm between dilutions. The change in absorption at 300 nm is plotted against the calculated $Ca^{2+}$ concentrations to arrive at a dissociation constant of 0.45 μM for the BAPTA dextran conjugate.

Example 40. Chelation of a fluorescent polycation. Terbium (111) chloride is mixed with ~10,000 MW BAPTA dextran (Compound XXVI) and the product is separated from free $Tb^{3+}$ by elution on a column of Sephadex G-10. Fluorescence of the chelated metal at ~490 nm and ~550 nm is detected by excitation at 280 nm. Similar techniques can be used to prepare radionuclide conjugates of the ION—SELECTIVE POLYMERS from polycations such as $^{45}Ca^{2+}$, $^{153}Gd^{3+}$ and $^{111}In^{3+}$.

Example 41. Ion binding to a conjugate of a reactive BAPTA with one blue fluorescent (indolyl) dye and a water-in, soluble polymer linked by an ether and a carboxamide group (Compound XXXVI). The agarose conjugate of the indolyl BAPTA whose preparation is described in Example 36 is loaded into a 5 mL column to give a wet bed volume of approximately 1 mL indo agarose. When exposed to short wavelength UV light, the column fluoresces light blue. A solution of 0.5 mL 10 mmoles $CaCl_2$ is loaded onto the column and eluted with deionized water. The portion of the column which binds $Ca^{2+}$ becomes green fluorescent green and is easily distinguishable from the unbound portion of the column which remains blue fluorescent. The emission change is easily monitored with a hand held UV lamp. The amount of $Ca^{2+}$ bound to the column can be determined by measuring the volume of gel that binds $Ca^{2+}$ and multiplying by the degree of substitution. In this example, if 0.7 mL of the indo-labeled agarose is bound to $Ca^{2+}$ and there is 7 µM of indicator per milliliter of agarose, then there was 5 µM of $Ca^{2+}$ in the ion containing solution. Elution of the column with three column volumes of 2% HCl removes the bound metal and regenerates the column. In acid, the column visibly changes color, from cream to a yellow. Washing with three column volumes of water at pH 7.5 removes excess acid and regenerates the column for reuse.

Example 42. Determining the capacity of a water-insoluble ion selective polymer. The number of BAPTA molecules covalently bound to the polystyrene resin, as synthesized in Example 26 is determined by measuring the absorbance of a solution of $CuCl_2$ (at 810 nm) before and after passing through a 1 g column of BAPTA resin. By this method, the number of binding sites is ~0.3 mmoles/gram dry resin. The binding capacity of conjugates of BAPTA linked to a polymer is also readily determined by atomic absorption measurements. In most cases the metal ion of interest can be separated from the polymer before analysis by elution with 2% HCl. Certain ions can also be quantitated using ion-selective electrodes.

Example 43. Calcium binding affinity of a water-insoluble ion selective polymer. To test the $Ca^{2+}$ binding affinity of a conjugate of BAPTA linked to a water-insoluble polymer such as Compound XXX, the same volume (3 mL) of three solutions with $CaCl_2$ concentrations of 10, 100 and 500 µM are passed over separate 1 mL columns of water-insoluble polymer and the final $Ca^{2+}$ concentration measured in a fluorimeter with the highly sensitive fluorescent $Ca^{2+}$ indicator, fura-2 [U.S. Pat. No. 4,603,209]. The ratio of the excitation intensities at 342 nm and 384 nm is measured before and after ion depletion. The measured ratios are compared to a standard curve of the $^{342}/_{384}$ nm ratio of fura-2 over a range of $Ca^{2+}$ concentrations, to graphically arrive at the concentration of free $Ca^{2+}$ remaining. This test shows that 1 g of the conjugate of BAPTA linked to a water-insoluble polymer described in Example 2 depletes all three samples to approximately $40 \times 10^{-9}$ M. This appears to be the limit of depletion, although the limited sensitivity of $Ca^{2+}$ detection with fura-2 at this low level of $Ca^{2+}$ and any trace contamination will result in errors in measuring these extremely low levels of $Ca^{2+}$.

Figure 9:
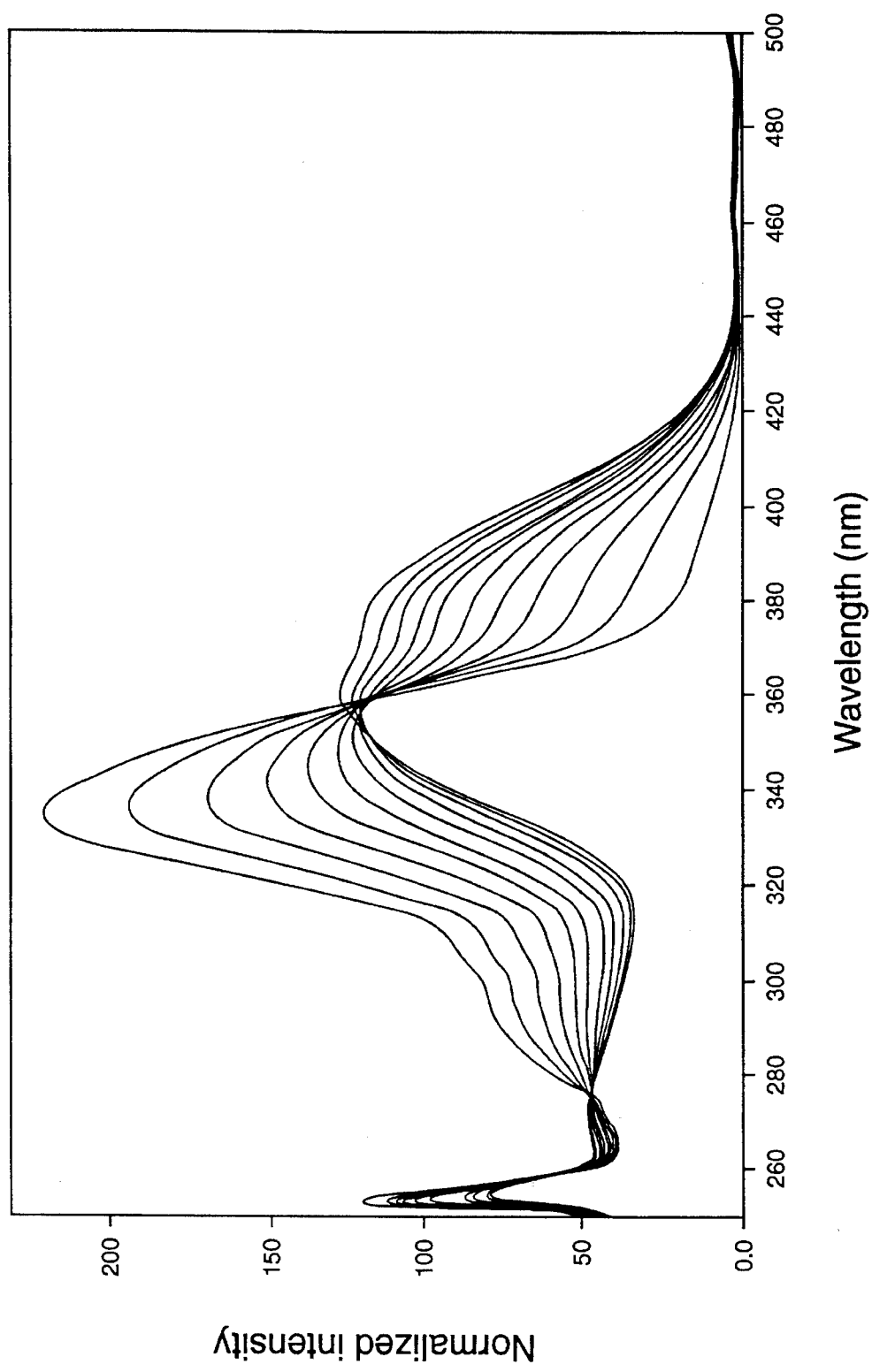
FIG. 9: Calcium Response of Compound XLIV: The excitation response of this fluorescent, water soluble indicator conjugate is described in Example 44

Example 44. Calcium binding affinity of a water soluble BAPTA conjugate with one green fluorescent (oxazolyl-furan) dye. The affinity of a fluorescent BAPTA compound conjugate is determined by dissolving 5 mg of the labeled dextran (Compound XLIV) in 1 ml deionized water and diluting 50 µL into three milliliters each of the Calcium Calibration Buffer Kit II (Molecular Probes Inc, Eugene, Oreg.) and cross diluting as in Example 38. The excitation of the dye solutions are scanned between dilutions while collecting the emission at 510 nm. The excitation response is similar to that of the free fura-2 (FIG. 9).

Example 45. Determining the degree of labeling for a water soluble BAPTA conjugate with one green fluorescent (oxazolyl-furan) dye. A 50 µL aliquot of the stock solution from Example 44 is diluted into three milliliters of each of the two calcium buffers as in Example 38 and the absorption spectra of the two solutions are scanned. The degree of labelling is then calculated by a comparison of the extinction coefficient of the labelled dye with that of the free dye. In this way, the number of dyes covalently bound to an average molecular weight dextran can be determined. The degree of substitution of the dextran conjugate synthesized in Example 34 (Compound XLIV) is 9.3 dyes/70,000 MW dextran.

It is to be understood that, while the foregoing invention has been described in detail by way of illustration and example, numerous modifications, substitutions, and alterations are possible without departing from the spirit and scope of the invention as described in the following claims.

What is claimed is:

1. A compound of the formula:

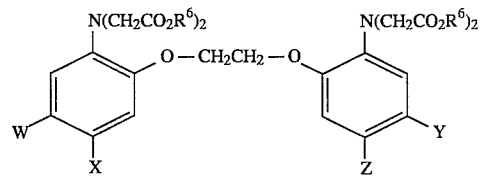

where both of W and X, which may be the same or different, are functional groups of the formula $(R^1)_n(R^2)$, wherein n=0 or 1;

$R^1$ is a spacer that is —$OCH_2R^3$—, —$OR^3$—, —$SR^3$—, —$SR^{3'}$—, —$NHCOCH_2R^3$—, —$NHCOR^{3'}$—, —$CONHCH_2R^3$—, —$CONHR^3$—, —$NHSO_2R^3$—, —$NHSO_2R^{3'}$—, —$NHCONHCH_2R^3$—, —$NHCONHR^{3'}$—, —$NHCSNHCH_2R^3$—, or —$NHCSNHR^3$—, where $R^3$ is $(CH_2)_m$ and m=1–18, and $R^{3'}$ is phenylene (—$C_6H_4$—); and $R^2$ is a reactive terminus that is an alcohol or phenol, a thiol, a haloacetamide, an alkyl halide, an alkyl sulfonate, an amine or aniline, a carboxylic acid, an anhydride, an isocyanate, an isothiocyanate, a maleimide, or an activated ester; or one of W and X is a functional group of the formula $(R^1)_n(R^2)$ in any of its described variations, and the other of W and X is H, $CH_3$, $NO_2$, $CF_3$, F, Cl, Br, I, or contains a fluorophore according to the formula:
$(R^a)_{n''}(R^b)_{n'}$-FLUOR, wherein n"=0 or 1; $R^a$ is —$OCH_2R^3$—, —$OR^3$—, —$SR^3$—, —$SR^{3'}$—, —$NHCOCH_2R^3$—, —$NHCOR^{3'}$—, —$CONHCH_2R^3$—, —$CONHR^3$—, —$NHSO_2R^3$—, —$NHSO_2R^{3'}$—, —$NHCONHCH_2R^3$—, —$NHCONHR^{3'}$—, —$NHCSNHCH_2R^3$—, or —$NHCSNHR^3$—, where $R^3$ is $(CH_2)_m$ and m=1–18, and $R^{3'}$ is phenylene (—$C_6H_4$—);

$R^b$ is —NH—, —NHCO—, —NHCS—, —S—, —O—, —CO—; or —$CH_2$— or —$COCH_2$—, or succinimidyl, and n'=0 or 1; and -FLUOR is an aromatic oxygen heterocycle fluorophore, or a 2-indolyl or carboxy substituted 2-indolyl, provided that when -FLUOR is a 2-indolyl or a carboxy substituted 2-indolyl fluorophore, n" and n' are 0; or —$OR^5$, —$CO_2R^5$, or —$OCH_2CO_2R^5$, where $R^5$ is an alkyl group with 1–5 carbons, a benzyl ($C_6H_5CH_2$—), an alpha-acyloxyalkyl or a pharmaceutically acceptable esterifying group, or a pharmaceutically acceptable salt; and Y and Z, which may be the same or different, are independently H, $CH_3$, $NO_2$, $CF_3$, F, Cl, Br, I, —$OR^5$, —$CO_2R^5$, or —$OCH_2CO_2R^5$, where $R^5$ is an alkyl group with 1–5 carbons, a benzyl, an alpha-acyloxyalkyl or a pharmaceutically acceptable esterifying group, or a pharmaceutically acceptable salt; a functional group of the formula $(R^1)_n(R^2)$, in any of its described variations; or contains a fluorophore according to the formula:

$(R^a)_{n''}(R^b)_{n'}$-FLUOR, wherein n''=0 or 1; $R^a$ is —OCH$_2$R$^3$—, —OR$^{3'}$—, —SR$^3$—, —SR$^{3'}$—, —NHCOCH$_2$R$^3$—, —NHCOR$^{3'}$—, —CONHCH$_2$R$^3$—, —CONHR$^{3'}$—, —NHSO$_2$R$^3$—, —NHSO$_2$R$^{3'}$—, —NHCONHCH$_2$R$^3$—, —NHCONHR$^{3'}$—, —NHCSNHCH$_2$R$^3$—, or —NHCSNHR$^{3'}$—, where $R^3$ is $(CH_2)_m$ and m=1–18, and $R^{3'}$ is phenylene (—C$_6$H$_4$—); $R^b$ is —NH—, —NHCO—, —NHCS—, —S—, —O—, —CO—; or —CH$_2$— or —COCH$_2$—, or succinimidyl, and n'=0 or 1; and -FLUOR is an aromatic oxygen heterocycle fluorophore, or a 2-indolyl or carboxy substituted 2-indolyl, provided that when -FLUOR is a 2-indolyl or a carboxy substituted 2-indolyl fluorophore, n'' and n' are 0;

or combinations thereof;

or Y taken together with Z and the aromatic carbons at the 4' and 5' positions form a benzofuran or oxazolyl-substituted or carboxy-oxazolyl substituted benzofuran fluorophore; and $R^6$ is an alkyl group with 1–5 carbons, a benzyl, an alpha-acyloxyalkyl or a pharmaceutically acceptable esterifying group, or a pharmaceutically acceptable salt.

2. A compound as claimed in claim 1, wherein the reactive terminus ($R^2$) of any functional group, which may be the same or different, is optionally —NH$_2$, —NCO, —NCS, —SH, —OH, maleimidyl (—NC$_4$H$_2$O$_2$); —CH$_2$Q or —NHCOCH$_2$Q, where Q is Cl, Br, I, methane sulfonyloxy, p-toluenesulfonyloxy, or trifluoromethanesulfonyloxy; or —COR$^7$ or —O(CH$_2$)COR$^7$, where $R^7$ is Cl, —OH, oxysuccinimidyl (—ONC$_4$H$_4$O$_2$), -1-oxybenzotriazolyl (—OC$_6$H$_4$N$_3$); or a phenoxy or phenoxy substituted one or more times by substituents that are nitro, fluoro, chloro, cyano, or trifluoromethyl, or combinations thereof; or —OCOR$^8$ or —OC(=NR$^8$)—NHR$^9$, where $R^8$ and $R^9$, which may be the same or different, are C$_1$—C$_6$ alkyl, perfluoroalkyl, or alkoxy; or cyclohexyl, 3-dimethylaminopropyl, or N-morpholinoethyl.

3. A fluorescent ion-selective conjugate with a carrier having the formula:

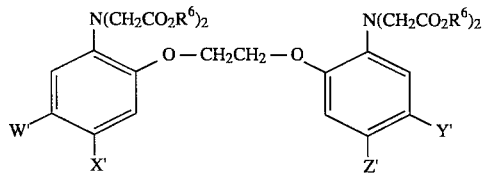

where at least one of W' and X' contains -POLY that is attached by a covalent linkage that is an ether, a thioether, a carboxamide, a sulfonamide, an alkyl amide, a urea or a thiourea linkage, where -POLY is a biologically compatible polymolecular assembly with a molecular weight greater than about 750 Daltons;

and at least one of X' and Z' contains a fluorophore according to the formula:

$(R^a)_n(R^b)_{n'}$-FLUOR, wherein n=0 or 1; $R^a$ is —OCH$_2$R$^3$—, —OR$^{3'}$—, —SR$^3$—, —SR$^{3'}$—, —NHCOCH$_2$R$^3$—, —NHCOR$^{3'}$—, —CONHCH$_2$R$^3$—, —CONHR$^{3'}$—, —NHSO$_2$R$^3$—, —NHSO$_2$R$^{3'}$—, —NHCONHCH$_2$R$^3$—, —NHCONHR$^{3'}$—, —NHCSNHCH$_2$R$^3$—, or —NHCSNHR$^{3'}$—, where $R^3$ is $(CH_2)_m$ and m=1–6, and $R^{3'}$ is phenylene (—C$_6$H$_4$—);

$R^b$ is —NH—, —NHCO—, —NHCS—, —S—, —O—, —CO—; or —CH$_2$— or —COCH$_2$—, or succinimidyl, and n'=0 or 1; and -FLUOR is an aromatic oxygen heterocycle fluorophore, or a 2-indolyl or a carboxy substituted 2-indolyl fluorophore, provided that when -FLUOR is a 2-indolyl or a carboxy substituted 2-indolyl fluorophore, n and n' are 0;

or Z' taken together with Y' and the aromatic carbons at the 4' and 5' positions form a benzofuran or oxazolyl-substituted or carboxy-oxazolyl substituted benzofuran fluorophore;

the remainder of substituents W', X', Y', and Z', which may be the same or different, are independently H, CH$_3$, NO$_2$, CF$_3$, F, Cl, Br, I, —OR$^5$, —CO$_2$R$^5$, or —OCH$_2$CO$_2$R$^5$, where $R^5$ is an alkyl group with 1–5 carbons, a benzyl (C$_6$H$_5$CH$_2$—), an alpha-acyloxyalkyl or a pharmaceutically acceptable esterifying group, or a pharmaceutically acceptable salt;

$(R^a)_n(R^b)$-POLY, in any of its described variations; or $(R^a)_n(R^b)_{n'}$-FLUOR, in any of its described variations; or combinations thereof; and $R^6$ is an alkyl group with 1–5 carbons, a benzyl, an alpha-acyloxyalkyl or a pharmaceutically acceptable esterifying group, or a pharmaceutically acceptable salt.

4. A conjugate, as claimed in claim 3, wherein -FLUOR is a fluorescein, a rhodamine, a coumarin, or a 2-indolyl or a carboxy substituted 2-indolyl fluorophore.

5. A fluorescent ion-selective compound having the formula:

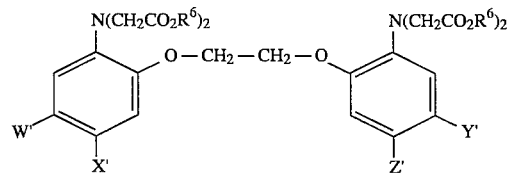

where at least one of W', X', Y' and Z' contains a fluorophore conjugate -FLUOR' that is attached to the compound by a covalent linkage that is an ether, thioether, sulfonamide, carboxamide, alkyl amine, urea, or thiourea linkage, according to the formula: $(R^a)_n(R^b)$-FLUOR', wherein n=0 or 1; $R^a$ is —OCH$_2$R$^3$—, —OR$^{3'}$—, —SR$^3$—, —SR$^{3'}$—, NHCOCH$_2$R$^3$—, —NHCOR$^{3'}$—, —CONHCH$_2$R$^3$—, —CONHR$^{3'}$—, NHSO$_2$R$^3$—, —NHSO$_2$R$^{3'}$—, —NHCONHCH$_2$R$^3$—, —NHCONHR$^{3'}$—, —NHCSNHCH$_2$R$^3$—, or —NHCSNHR$^{3'}$—, where $R^3$ is $(CH_2)_m$ and m=1–6, and $R^{3'}$ is phenylene (—C$_6$H$_4$—); $R^b$ is —NH—, —NHCO—, —NHCS—, —S—, —O—, —CO—; or —CH$_2$— or —COCH$_2$—,

31 or succinimidyl; and -FLUOR' is a fluorescein, rhodamine or coumarin fluorophore; and the remainder of substituents W', X', Y', and Z', which may be the same or different, are independently H, $CH_3$, $NO_2$, $CF_3$, F, Cl, Br, I, $-OR^5$, $-CO_2R^5$, or $-OCH_2CO_2R^5$, where $R^5$ is an alkyl group with 1–5 carbons, a benzyl ($C_6H_5CH_2-$), an alpha-acyloxyalkyl or a pharmaceutically acceptable esterifying group, or a pharmaceutically acceptable salt;

or contains an additional fluorophore -FLUOR that is attached to the compound by a covalent linkage that is an ether, thioether, sulfonamide, carboxamide, alkylamine, urea, or thiourea linkage or a single covalent bond, according to the formula: $(R^a)_n(R^b)_{n'}$-FLUOR, wherein n=0 or 1; $R^a$ is $-OCH_2R^3-$, $-OR^{3'}-$, $-SR^3-$, $-SR^{3'}-$, $NHCOCH_2R^3-$, $-NHCOR^{3'}-$, $-CONHCH_2R^3-$, $-CONHR^{3'}-$, $-NHSO_2R^3-$, $-NHSO_2R^{3'}-$, $-NHCONHCH_2R^3-$, $-NHCONHR^{3'}-$, $-NHCSNHCH_2R^3-$, or $-NHCSNHR^{3'}-$, where $R^3$ is $(CH_2)_m$ and m=1–6, and $R^{3'}$ is phenylene ($-C_6H_4-$); $R^b$ is $-NH-$, $-NHCO-$, $-NHCONH-$, $-NHCS-$, $-NHCSNH-$, $-NHSO_2-$, $-S-$, $-O-$, $-CO-$; or $-CH_2-$ or $-COCH_2-$, or succinimidyl, and n'=0 or 1; and -FLUOR is a fluorescein rhodamine or coumarin fluorophore, a 2-indolyl or a carboxy substituted 2-indolyl fluorophore, provided that when -FLUOR is a 2-indolyl or a carboxy, substituted 2-indolyl fluorophore, the linkage is a single covalent bond;

or Z' taken together with Y' and the aromatic carbons at the 4' and 5' positions form a benzofuran or oxazolyl-substituted or carboxy-oxazolyl substituted benzofuran fluorophore; or combinations thereof; and $R^6$ is an alkyl group with 1–5 carbons, a benzyl, an alpha-acyloxyalkyl or a pharmaceutically acceptable esterifying group, or a pharmaceutically acceptable salt.

6. A non-fluorescent ion-selective conjugate with a carrier having the formula:

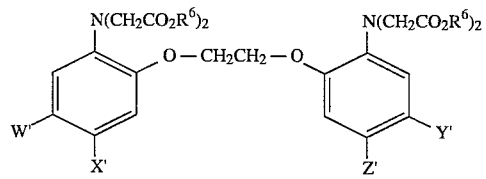

where at least one of W', X', Y', and Z' contains -POLY that is attached by a covalent linkage that is an ether, a thioether, a carboxamide, a sulfonamide, an alkyl amide, a urea or a thiourea linkage, where -POLY is a polymolecular assembly with a molecular weight greater than about 750 Daltons;

the remainder of substituents W', X', Y', and Z', which may be the same or different, are independently H, $CH_3$, $NO_2$, $CF_3$, F, Cl, Br, I, $-OR^5$, $-CO_2R^5$, or $-OCH_2CO_2R^5$, where $R^5$ is an alkyl group with 1–5 carbons, a benzyl ($C_6H_5CH_2-$), an alpha-acyloxyalkyl or a pharmaceutically acceptable esterifying group, or a pharmaceutically acceptable salt; or $(R^a)_{n''}(R^b)_{n'}$-POLY,

32 in any of its described variations; or combinations thereof; and $R^6$ is an alkyl group with 1–5 carbons, a benzyl, an alpha-acyloxyalkyl or a pharmaceutically acceptable esterifying group, or a pharmaceutically acceptable salt.

7. A compound, as claimed in claim 2, wherein one of W and X is a functional group of the formula $(R^1)_n(R^2)$.

8. A compound, as claimed in claim 7, wherein one of W and X is a functional group of the formula $(R^1)_n(R^2)$, where n=0 or 1, and $R^1$ is $-O(CH_2)_m-$, m=1–18; $R^2$ is $-NH_2$, $-NCS$, $-CH_2Q$, $-NHCOCH_2Q$, or $-COR^7$, where Q is Cl, Br or I and where $R^7$ is Cl, $-OH$, or oxysuccinimidyl ($-ONC_4H_4O_2$).

9. A compound, as claimed in claim 8, wherein X is $-NH_2$.

10. A compound, as claimed in claim 8, wherein X is $-NCS$.

11. A compound, as claimed in claim 8, wherein X is $-CH_2Q$ or $-NHCOCH_2Q$.

12. A compound, as claimed in claim 8, wherein W is $(R^1)_n(R^2)$, $R^1$ is $-O(CH_2)_m-$ and $R^2$ is $-COR^7$, where $R^7$ is Cl, $-OH$, or oxysuccinimidyl ($-ONC_4H_4O_2$).

13. A compound, as claimed in claim 12, wherein one of Y and Z is H, $CH_3$, $NO_2$, $CF_3$, F, Cl, Br, I, $-OR^5$, $-CO_2R^5$, or $-OCH_2CO_2R^5$, where $R^5$ is an alkyl group with 1–5 carbons or a benzyl ($C_6H_5CH_2-$); and the other of Y and Z is H.

14. A compound, as claimed in claim 9, wherein Z is $-NH_2$ and W and Y are H.

15. A compound, as claimed in claim 10, wherein Z is $-NH_2$ and W and Y are H.

16. A compound, as claimed in claim 7, wherein the other of W or X contains a fluorophore according to the formula: $(R^a)_{n''}(R^b)_{n'}$-FLUOR, where n''=0; or Z contains a fluorophore according to the formula: $(R^a)_{n''}(R^b)_{n'}$-FLUOR, where n''=0; and remaining substituents are independently H, $CH_3$, $NO_2$, $CF_3$, F, Cl, Br, I, $-OR^5$, $-CO_2R^5$, or $-OCH_2CO_2R^5$, where $R^5$ is an alkyl group with 1–5 carbons or a benzyl ($C_6H_5CH_2-$).

17. A compound, as claimed in claim 16, wherein -FLUOR is an aromatic oxygen heterocycle fluorophore that is a fluorescein, a naphthofluorescein, a seminaphthofluorescein, a rhodol, a rhodamine, a rosamine or a coumarin.

18. A compound, as claimed in claim 16, wherein one of X or Z contains a fluorophore according to the formula: $(R^a)_{n''}(R^b)_{n'}$-FLUOR, wherein $R^b$ is $-NH-$, $-NHCO-$, or $-NHCS-$.

19. A compound, as claimed in claim 18, wherein -FLUOR is a naphthofluorescein, a semi-naphthofluorescein, a rhodol, an eosin, an erythrosin, a tetrachlorofluorescein, a dichlorofluorescein, a tetramethylrhodamine, a rhodamine -B, -6G, -101, -110, -123, or -X, a sulfonamide of sulfo rhodamine 101, a rosamine, a hydroxycoumarin, an alkoxy coumarin, a dialkylaminocoumarin or a trifluoromethyl coumarin.

20. A compound, as claimed in claim 17, where W is a functional group of the formula $(R^1)_n(R^2)$, wherein $R^1$ is $-O(CH_2)_m-$, m=1–18, and $R^2$ is $-COR^7$, where $R^7$ is Cl, $-OH$, or oxysuccinimidyl ($-ONC_4H_4O_2$).

21. A compound, as claimed in claim 20, where W is $-OCH_2COR^7$, where $R^7$ is oxysuccinimidyl ($-ONC_4H_4O_2$);

X or Z contains a fluorophore according to the formula: $(R^a)_{n''}(R^b)_{n'}$-FLUOR, wherein $R^b$ is $-NH-$, $-NHCO-$, or $-NHCS-$; and -FLUOR is a 2',7'- dichlorofluorescein, a tetramethylrhodamine, or a sulfonamide of sulforhodamine 101; such that when Z contains a fluorophore, X is H and when X contains a fluorophore, Z is $CH_3$; and Y is H.

22. A compound, as claimed in claim 19, wherein X is a functional group of the formula $(R^1)_n(R^2)$, wherein n=0 or 1, $R^1$ is $—O(CH_2)_m—$, m=1–18; $R_2$ is $—NH_2$, $—NCS$, $—CH_2Q$, $—NHCOCH_2Q$, or $—COR^7$; where Q is Cl, Br or I and $R^7$ is Cl, $—OH$, or oxysuccinimidyl ($—ONC_4H_4O_2$) and where Z contains a fluorophore.

23. A compound, as claimed in claim 22, wherein X is $—NH_2$, $—NCS$, $—NHCOCH_2Q$ or $CH_2Q$; and Z contains a fluorophore that is a 2',7'-dichlorofluorescein, a tetramethylrhodamine, or a sulfonamide of sulforhodamine 101.

24. A compound, as claimed in claim 16, wherein -FLUOR is a 2-indolyl or carboxy substituted 2-indolyl fluorophore.

25. A compound, as claimed in claim 24, wherein one of W and X is a functional group of the formula $(R^1)_n(R^2)$, where n=0 or 1, and $R^1$ is $—O(CH_2)_m—$, m=1–18; $R^2$ is $—NH_2$, $—NCS$, $—CH_2Q$, $—NHCOCH_2Q$, or $—COR^7$, where Q is Cl, Br or I and where $R^7$ is Cl, $—OH$, or oxysuccinimidyl ($—ONC_4H_4O_2$).

26. A compound, as claimed in claim 25, wherein W is $—O(CH_2)COR^7$, where $R^7$ is Cl, $—OH$, or oxysuccinimidyl ($—ONC_4H_4O_2$), and X or Z contains the 2-indolyl or carboxy substituted 2-indolyl fluorophore.

27. A compound, as claimed in claim 25, wherein X is $—NH_2$, $—NCS$, $—NHCOCH_2Q$ or $—CH_2Q$; and Z contains a 2-indolyl or carboxy substituted 2-indolyl fluorophore.

28. A compound, as claimed in claim 7, wherein Y taken together with Z and the aromatic carbons at the 4' and 5' positions form a benzofuran or an oxazolyl-substituted or carboxy-oxazolyl substituted benzofuran fluorophore.

29. A compound, as claimed in claim 28, wherein one of W and X is a functional group of the formula $(R^1)_n(R^2)$, where n=0 or 1, and $R^1$ is $—O(CH_2)_m—$, m=1–18; $R^2$ is $—NH_2$, $—NCS$, $—CH_2Q$, $—NHCOCH_2Q$, or $—COR^7$, where Q is Cl, Br or I and where $R^7$ is Cl, $—OH$, or oxysuccinimidyl ($—ONC_4H_4O_2$); and the other of W and X is H, $CH_3$, $NO_2$, $CF_3$, F, Cl, Br, I, $—OR^5$, $—CO_2R^5$, or $—OCH_2CO_2R^5$, where $R^5$ is an alkyl group with 1–5 carbons or a benzyl ($C_6H_5CH_2—$).

30. A compound, as claimed in claim 29, wherein X is $—NH_2$, $—NCS$, $—NHCOCH_2Q$ or $—CH_2Q$.

31. A compound, as claimed in claim 29, wherein W is $—O(CH_2)COR^7$, where $R^7$ is Cl, $—OH$, or oxysuccinimidyl ($—ONC_4H_4O_2$).

32. A compound, as claimed in claim 7, wherein one of Y and Z is a functional group of the formula $(R^1)_n(R^2)$.

33. A compound, as claimed in claim 8, wherein one of Y and Z is a functional group of the formula $(R^1)_n(R^2)$, where n=0 or 1, and $R^1$ is $—O(CH_2)_m—$, m=1–18; $R^2$ is $—NH_2$, $—NCS$, $—CH_2Q$, $—NHCOCH_2Q$, or $—COR^7$, where Q is Cl, Br or I and where $R^7$ is Cl, $—OH$, or oxysuccinimidyl ($—ONC_4H_4O_2$); and the other of Y and Z is H, $CH_3$, $NO_2$, $CF_3$, F, Cl, Br, I, $—OR^5$, $—CO_2R^5$, or $—OCH_2CO_2R^5$, where $R^5$ is an alkyl group with 1–5 carbons or a benzyl ($C_6H_5CH_2—$).

34. A compound, as claimed in claim 33, wherein W is $—O(CH_2)COR^7$, where $R^7$ is Cl, $—OH$, or oxysuccinimidyl ($—ONC_4H_4O_2$); and X or Z is $—NH_2$, $—NCS$, $—NHCOCH_2Q$ or $—CH_2Q$.

35. A conjugate, as claimed in claim 3, wherein -POLY is a biologically compatible polymolecular assembly with a molecular weight between about 1000 and about 10,000,000 Daltons.

36. A conjugate, as claimed in claim 3, wherein W' or X' contains -POLY that is a synthetic polymeric resin or gel; glass; polyol; polysaccharide; polypeptide or protein; or naturally or chemically cross-linked forms thereof; or a natural or synthetic liposome or micelle.

37. A conjugate, as claimed in claim 3, wherein -POLY is a polysaccharide.

38. A conjugate, as claimed in claim 35, wherein -POLY is a dextran.

39. A conjugate, as claimed in claim 3, wherein one of X' or Z' contains a fluorophore according to the formula: $(R^a)_n(R^b)_n$-FLUOR, where -FLUOR is a naphthofluorescein, a semi-naphthofluorescein, a rhodol, an eosin, an erythrosin, a tetrachlorofluorescein, a dichlorofluorescein, a tetramethylrhodamine, a rhodamine -B, -6G, -101, -110, -123, or -X, a sulfonamide of sulfo rhodamine 101, a rosamine, a hydroxycoumarin, an alkoxy coumarin, a dialkylaminocoumarin or a trifluoromethyl coumarin.

40. A conjugate, as claimed in claim 3, wherein one of X' or Z' contains a fluorophore according to the formula: $(R^a)_n(R^b)_n$-FLUOR, wherein -FLUOR is a 2-indolyl or carboxy substituted 2-indolyl fluorophore.

41. A conjugate, as claimed in claim 3, wherein Z' taken together with Y' and the aromatic carbons at the 4' and 5' positions form a benzofuran or oxazolyl-substituted or carboxy-oxazolyl substituted benzofuran fluorophore.

42. A conjugate, as claimed in claim 3, wherein X' or Z' contains a fluorophore according to the formula: $(R^a)_n(R^b)_n$-FLUOR, wherein n=0.

43. A conjugate, as claimed in claim 42, wherein -FLUOR is a 2',7'-dichlorofluorescein, a tetramethylrhodamine, or a sulfonamide of sulforhodamine 101.

44. A conjugate, as claimed in claim 43, wherein $R^b$ is $—NH—$, $—NHCO—$, or $—NHCS—$.

45. A conjugate, as claimed in claim 3, wherein W' or X' has the formula:

$(R^a)_n(R^b)$-POLY, wherein n=0 or 1;
$R^a$ is $—OCH_2R^3—$, $—OR^{3'}—$, $—SR^3—$, $—SR^{3'}—$,
$—NHCOCH_2R^3—$, $—NHCOR^{3'}—$,
$—CONHCH_2R^3—$, $—CONHR^{3'}—$,
$—NHSO_2R^3—$, $—NHSO_2R^{3'}—$,
$—NHCONHCH_2R^3—$, $—NHCONHR^{3'}—$,
$—NHCSNHCH_2R^3—$, or $—NHCSNHR^{3'}—$, where $R^3$ is $(CH_2)_m$ and m=1–18, and $R^{3'}$ is phenylene ($—C_6H_4—$);
$R^b$ is $—NH—$, $—NHCO—$, $—NHCS—$, $—S—$, $—O—$, $—CO—$, $—CH_2—$, $—COCH_2—$, or a succinimidyl.

46. A conjugate, as claimed in claim 45, wherein -POLY is a polysaccharide and Z' contains a fluorophore according to the formula:

$(R^a)_n(R^b)_n$-FLUOR, wherein n=0, and -FLUOR is a naphthofluorescein, a semi-naphthofluorescein, a rhodol, an eosin, an erythrosin, a tetrachlorofluorescein, a dichlorofluorescein, a tetramethylrhodamine, a rhodamine -B, -6G, -101, -110, -123, or -X, a sulfonamide of sulfo rhodamine 101, a rosamine, a hydroxycoumarin, an alkoxy coumarin, a dialkylaminocoumarin or a trifluoromethyl coumarin; and the remaining substituents are H, $CH_3$, $NO_2$, $CF_3$, F, Cl, Br, I, $—OR^5$, $—CO_2R^5$, or $—OCH_2CO_2R^5$, where $R^5$ is an alkyl group with 1–5 carbons or a benzyl ($C_6H_5CH_2—$).

47. A conjugate, as claimed in claim 45, wherein -POLY is a polysaccharide; Z' contains a fluorophore according to the formula:

$(R^a)_n(R^b)_n$-FLUOR, wherein -FLUOR is 2-indolyl or carboxy substituted 2-indolyl fluorophore; and the remaining substituents are H, $CH_3$, $NO_2$, $CF_3$, F, Cl, Br, I, —$OR^5$, —$CO_2R^5$, or —$OCH_2CO_2R^5$, where $R^5$ is an alkyl group with 1–5 carbons or a benzyl ($C_6H_5CH_2$—).

48. A conjugate, as claimed in claim 45, wherein -POLY is a polysaccharide; Z' taken together with Y' and the aromatic carbons at the 4' and 5' positions form a benzofuran or oxazolyl-substituted or carboxy-oxazolyl substituted benzofuran fluorophore; and the remaining substituents are H, $CH_3$, $NO_2$, $CF_3$, F, Cl, Br, I, —$OR^5$, —$CO_2R^5$, or —$OCH_2CO_2R^5$, where $R^5$ is an alkyl group with 1–5 carbons or a benzyl ($C_6H_5CH_2$—).

49. A conjugate, as claimed in claim 45, wherein W' contains -POLY that is a polysaccharide; X' contains a fluorophore according to the formula:

$(R^a)_n(R^b)_n$-FLUOR, wherein n=0 and -FLUOR is a naphthofluorescein, a semi-naphthofluorescein, a rhodol, an eosin, an erythrosin, a tetrachlorofluorescein, a dichlorofluorescein, a tetramethylrhodamine, a rhodamine -B, -6G, -101, -110, -123, or -X, a sulfonamide of sulfo rhodamine 101, a rosamine, a hydroxycoumarin, an alkoxy coumarin, a dialkylaminocoumarin or a trifluoromethyl coumarin; and the remaining substituents are H, $CH_3$, $NO_2$, $CF_3$, F, Cl, Br, I, —$OR^5$, —$CO_2R^5$, or —$OCH_2CO_2R^5$, where $R^5$ is an alkyl group with 1–5 carbons or a benzyl ($C_6H_5CH_2$—).

50. A conjugate, as claimed in claim 45, wherein Z' contains a fluorophore according to the formula:

$(R^a)_n(R^b)_n$-FLUOR, wherein -FLUOR is a 2-indolyl or a carboxy substituted 2-indolyl fluorophore; and the remaining substituents are H, $CH_3$, $NO_2$, $CF_3$, F, Cl, Br, I, —$OR^5$, —$CO_2R^5$, or —$OCH_2CO_2R^5$, where $R^5$ is an alkyl group with 1–5 carbons or a benzyl ($C_6H_5CH_2$—).

51. A compound, as claimed in claim 5, wherein X' contains a fluorophore -FLUOR' that is a naphthofluorescein, a semi-naphthofluorescein, a rhodol, an eosin, an erythrosin, a tetrachlorofluorescein, a dichlorofluorescein, a tetramethylrhodamine, a rhodamine -B, -6G, - 101,–110, –123, or -X, a sulfonamide of sulforhodamine 101, a rosamine, a hydroxycoumarin, an alkoxy coumarin, a dialkylaminocoumarin or a trifluoromethyl coumarin; and W' is H.

52. A compound, as claimed in claim 51, wherein FLUOR' is attached to the compound by a covalent linkage that is a carboxamide, sulfonamide, urea or thiourea linkage.

53. A compound, as claimed in claim 51, wherein Z' contains an additional fluorophore -FLUOR.

54. A compound, as claimed in claim 53, wherein Z' contains an additional fluorophore -FLUOR, where -FLUOR is a naphthofluorescein, a semi-naphthofluorescein, a rhodol, an eosin, an erythrosin, a tetrachlorofluorescein, a dichlorofluorescein, a tetramethylrhodamine, a rhodamine -B, -6G, - 101, -110, -123, or -X, a sulfonamide of sulforhodamine 101, a rosamine, a hydroxycoumarin, an alkoxy coumarin, a dialkylaminocoumarin or a trifluoromethyl coumarin.

55. A compound, as claimed in claim 53, wherein Z' contains an additional fluorophore -FLUOR, wherein -FLUOR is a 2-indolyl or carboxy substituted 2-indolyl fluorophore.

56. A compound, as claimed in claim 51, wherein Z' taken together with Y' and the aromatic carbons at the 4' and 5' positions form a benzofuran or oxazolyl-substituted or carboxy-oxazolyl substituted benzofuran fluorophore.

57. A conjugate, as claimed in claim 6, wherein -POLY is a synthetic polymeric resin or gel; glass; polyol; polysaccharide; polypeptide or protein; or naturally or chemically cross-linked forms thereof; or a natural or synthetic liposome or micelle.

58. A compound, as claimed in claim 5, wherein $R^6$ is an alpha-acyloxyalkyl or a pharmaceutically acceptable salt;

W' is H,

X' contains a fluorophore conjugate FLUOR' that is a fluorescein, rhodamine, or coumarin derivative and that is attached to the compound by a covalent linkage that is a carboxamide, sulfonamide, urea or thiourea linkage, and Y' and Z' are independently H, $CH_3$, $NO_2$, $CF_3$, F, Cl, Br, or I, or Z' contains an additional fluorophore FLUOR that is a fluorescein, rhodamine, or coumarin derivative and that is attached to the compound by a covalent linkage that is a carboxamide, sulfonamide, urea or thiourea linkage.

59. A compound, as claimed in claim 5, wherein X' contains a fluorophore conjugate according to the formula $(R^a)_n(R^b)$-FLUOR',wherein n=0.

60. A compound, as claimed in claim 59, wherein $R^b$ is —NHCO—, NHCONH—, NHCSNH— or —$NHSO_2$ —; and -FLUOR' is a 2',7'-dichlorofluorescein, a tetramethylrhodamine, or a sulfonamide of sulforhodamine 101.

61. A compound, as claimed in claim 5, wherein $R^6$ is an alpha-acyloxyalkyl or a pharmaceutically acceptable salt;

W' is H,

X' contains a fluorophore conjugate according to the formula $(R^a)_n(R^b)$-FLUOR', wherein n=0, $R^b$ is —NHCO—, —NHCONH—, —NHCS—, —NHCSNH—, $NHSO_2$—, and FLUOR' is a naphthofluorescein, a semi-naphthofluorescein, a rhodol, an eosin, an erythrosin, a tetrachlorofluorescein, a dichlorofluorescein, a tetramethylrhodamine, a rhodamine -B, -6G, -101, -110,-123, or -X, a sulfonamide of sulforhodamine 101, a rosamine, and Y' and Z' are independently H, $CH_3$, $NO_2$, $CF_3$, F, Cl, Br, or I, or Z' contains an additional fluorophore according to the formula $(R^a)_n(R^b)$-FLUOR, wherein n=0, $R^b$ is —NHCO—, —NHCONH—, —NHCS—, —NHCSNH—, or $NHSO_2$—, and FLUOR is the same as FLUOR'.

62. A compound, as claimed in claim 61, wherein X' contains a fluorophore conjugate FLUOR' that is attached to the compound according to the formula $(R^a)_n(R^b)$-FLUOR', wherein n=0 and $R^b$ is —NHCO—, —NHCSNH—, or $NHSO_2$—, and FLUOR' is a 2',7'-dichlorofluorescein;

W' and Y' are H; and

Z' is H, $CH_3$, $NO_2$, $CF_3$, F, Cl, Br, or I.

63. A compound, as claimed in claim 61, wherein X' contains a fluorophore conjugate FLUOR' that is attached to the compound according to the formula $(R^a)_n(R^b)$-FLUOR', wherein n=0 and $R^b$ is —NHCO—, —NHCSNH—, or $NHSO_2$—, and FLUOR' is a 2',7'-dichlorofluorescein;

W' and Y' are H; and

Z' contains an additional fluorophore according to the formula $(R^a)_n(R^b)$-FLUOR, wherein n=0 and $R^b$ is —NHCO—, —NHCSNH—, or NHSO$_2$—, and FLUOR is the same as FLUOR'.

64. A compound, as claimed in claim 61, wherein X' contains a fluorophore conjugate FLUOR' that is attached to the compound according to the formula $(R^a)_n(R^b)$-FLUOR', wherein n=0 and $R^b$ is —NHCO—, —NHCSNH—, or NHSO$_2$—, and FLUOR' is a tetramethylrhodamine;

W' and Y' are H; and

Z' is H, CH$_3$, NO$_2$, CF$_3$, F, Cl, Br, or I.

65. A compound, as claimed in claim 61, wherein X' contains a fluorophore conjugate FLUOR' that is attached to the compound according to the formula $(R^a)_n(R^b)$-FLUOR', wherein n=0 and $R^b$ is —NHCO—, —NHCSNH—, or NHSO$_2$—, and FLUOR' is a tetramethylrhodamine;

W' and Y' are H; and

Z' contains an additional fluorophore according to the formula $(R^a)_n(R^b)$-FLUOR, wherein n=0 and $R^b$ is —NHCO—, —NHCSNH—, or NHSO$_2$—, and FLUOR is the same as FLUOR'.

66. A compound, as claimed in claim 61, wherein X' contains a fluorophore conjugate FLUOR' that is attached to the compound according to the formula $(R^a)_n(R^b)$-FLUOR', wherein n=0 and $R^b$ is —NHCO—, —NHCSNH—, or NHSO$_2$—, and FLUOR' is a sulfonamide of sulforhodamine 101;

W' and Y' are H; and

Z' is H, CH$_3$, NO$_2$, CF$_3$, F, Cl, Br, or I.

67. A compound, as claimed in claim 61, wherein X' contains a fluorophore conjugate FLUOR' that is attached to the compound according to the formula $(R^a)_n(R^b)$-FLUOR', wherein n=0 and $R^b$ is —NHCO—, —NHCSNH—, or NHSO$_2$—, and FLUOR' is a sulfonamide of sulforhodamine 101;

W' and Y' are H; and

Z' contains an additional fluorophore according to the formula $(R^a)_n(R^b)$-FLUOR, wherein n=0 and $R^b$ is —NHCO—, —NHCSNH—, or NHS$_2$O —, and FLUOR is the same as FLUOR'.

* * * * *